US010925728B2

(12) United States Patent
Anderson et al.

(10) Patent No.: US 10,925,728 B2
(45) Date of Patent: Feb. 23, 2021

(54) PROSTHETIC HEART VALVE DELIVERY SYSTEMS AND METHODS

(71) Applicant: Medtronic Vascular, Inc., Santa Rosa, CA (US)

(72) Inventors: Marc A. Anderson, Galway (IE); Grainne Teresa Carroll, Galway (IE); Paul Devereux, Galway (IE); Niall Duffy, Galway (IE); Matthew Fleming, Roscommon (IE); Alexander J. Hill, Blaine, MN (US); Elliot J. Howard, Redwood City, CA (US); James R. Keogh, Maplewood, MN (US); Marian Patricia Lally, Galway (IE); Luke Lehmann, Newport Beach, CA (US); Jeffrey Madden, Galway (IE); Kevin M. Mauch, Windsor, CA (US); Ciaran McGuinness, Roscommon (IE); Brian T. McHenry, Golden Valley, MN (US); Karl L. Olney, Tustin, CA (US); Geoffrey Orth, Sebastopol, CA (US); Edward Sarnowski, Newport Coast, CA (US); Elizabeth A. Schotzko, Blaine, MN (US); Benjamin Wong, Irvine, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 16/282,885

(22) Filed: Feb. 22, 2019

(65) Prior Publication Data
US 2019/0254816 A1    Aug. 22, 2019

Related U.S. Application Data

(60) Provisional application No. 62/633,932, filed on Feb. 22, 2018.

(51) Int. Cl.
*A61F 2/24* (2006.01)

(52) U.S. Cl.
CPC .......... *A61F 2/2436* (2013.01); *A61F 2/2409* (2013.01); *A61F 2/2418* (2013.01);
(Continued)

(58) Field of Classification Search
CPC .......................................... A61F 2/2427–2439
See application file for complete search history.

(56) References Cited

U.S. PATENT DOCUMENTS 4,846,174 A    7/1989    Willard et al.
5,059,176 A   10/1991    Winters
(Continued)

FOREIGN PATENT DOCUMENTS

WO    2013/021374 A2    2/2013

OTHER PUBLICATIONS

PCT/US2019/019156, The International Search Report and Written Opinion, dated May 17, 2019, 14pages.
(Continued)

*Primary Examiner* — Rebecca S Preston
(74) *Attorney, Agent, or Firm* — Dicke, Billig & Czaja, PLLC

(57) ABSTRACT

Methods of transcatheter delivery of a prosthetic heart valve. A distal region of a guide member assembly is advanced into a heart of a patient. The distal region is docked to native anatomy of the heart. A delivery device, including a collapsed prosthetic heart valve, is advanced over the docked guide member assembly. The collapsed prosthetic heart valve is located at an implantation site. The prosthetic heart valve is deployed from the delivery device, and then the delivery device is removed from the patient. At least a portion of the guide member assembly is removed from the patient. In some embodiments, the docking structure is
(Continued)

docked to one or more of native mitral valve leaflets, chordae in the left ventricle, or walls of the left ventricle as part of a transseptal mitral valve delivery procedure.

23 Claims, 39 Drawing Sheets

(52) U.S. Cl.
CPC .......... *A61F 2/2427* (2013.01); *A61F 2/2454* (2013.01); *A61F 2/2412* (2013.01); *A61F 2/2433* (2013.01); *A61F 2/2466* (2013.01); *A61F 2210/0014* (2013.01); *A61F 2220/0008* (2013.01); *A61F 2220/0025* (2013.01); *A61F 2220/0075* (2013.01); *A61F 2250/006* (2013.01); *A61F 2250/0007* (2013.01); *A61F 2250/0039* (2013.01); *A61F 2250/0059* (2013.01)

(56) References Cited

U.S. PATENT DOCUMENTS

| | | | |
|---|---|---|---|
| 5,226,421 | A | 7/1993 | Frisbie et al. |
| 5,957,949 | A | 9/1999 | Leonhardt et al. |
| 6,562,031 | B2 | 5/2003 | Chandrasekaran et al. |
| 7,160,255 | B2 | 1/2007 | Saadat |
| 7,621,948 | B2 | 11/2009 | Herrmann et al. |
| 7,691,081 | B2 | 4/2010 | Crossman |
| 7,881,807 | B2 | 2/2011 | Schaer |
| 8,105,375 | B2 | 1/2012 | Navia et al. |
| 8,500,768 | B2 | 8/2013 | Cohen |
| 8,591,460 | B2 | 11/2013 | Wilson et al. |
| 9,078,994 | B2 | 7/2015 | Rosenman et al. |
| 2004/0210304 | A1 | 10/2004 | Sequin et al. |
| 2004/0260394 | A1 | 12/2004 | Douk et al. |
| 2008/0097294 | A1 | 4/2008 | Prather et al. |
| 2011/0208297 | A1 | 8/2011 | Tuval et al. |
| 2012/0016342 | A1 | 1/2012 | Brecker |
| 2012/0022640 | A1 | 1/2012 | Gross et al. |
| 2012/0059458 | A1 | 3/2012 | Buchbinder et al. |
| 2013/0035638 | A1 | 2/2013 | Thornton et al. |
| 2013/0060328 | A1 | 3/2013 | Rothstein |
| 2013/0226290 | A1 | 8/2013 | Yellin et al. |
| 2013/0231735 | A1 | 9/2013 | Deem et al. |
| 2013/0297010 | A1 | 11/2013 | Bishop et al. |
| 2013/0310928 | A1 | 11/2013 | Morriss et al. |
| 2014/0039611 | A1 | 2/2014 | Lane et al. |
| 2014/0142689 | A1* | 5/2014 | De Canniere ......... A61F 2/2457 623/2.11 |
| 2014/0180089 | A1 | 6/2014 | Alpert et al. |
| 2014/0350669 | A1 | 11/2014 | Gillespie et al. |
| 2014/0379074 | A1 | 12/2014 | Spence et al. |
| 2015/0051696 | A1* | 2/2015 | Hou ................. A61F 2/2427 623/2.11 |
| 2015/0119981 | A1 | 4/2015 | Khairkhahan et al. |
| 2015/0238315 | A1 | 8/2015 | Rabito et al. |
| 2015/0290432 | A1 | 10/2015 | Mathews et al. |
| 2015/0297346 | A1 | 10/2015 | Duffy et al. |
| 2015/0313738 | A1 | 11/2015 | Cully et al. |
| 2015/0320432 | A1 | 11/2015 | Adams |
| 2016/0022154 | A1 | 1/2016 | Warnking et al. |
| 2016/0027091 | A1 | 9/2016 | Ganesan et al. |

OTHER PUBLICATIONS

B. Faurie, "Rapid Pacing Using the Left Ventricular Guidewire: Reviving an Old Technique to Simplify BAV and TAVI Procedures", Catheterization and Cardiovascular Interventions 00:00-00 (2016) (6 pgs).

* cited by examiner

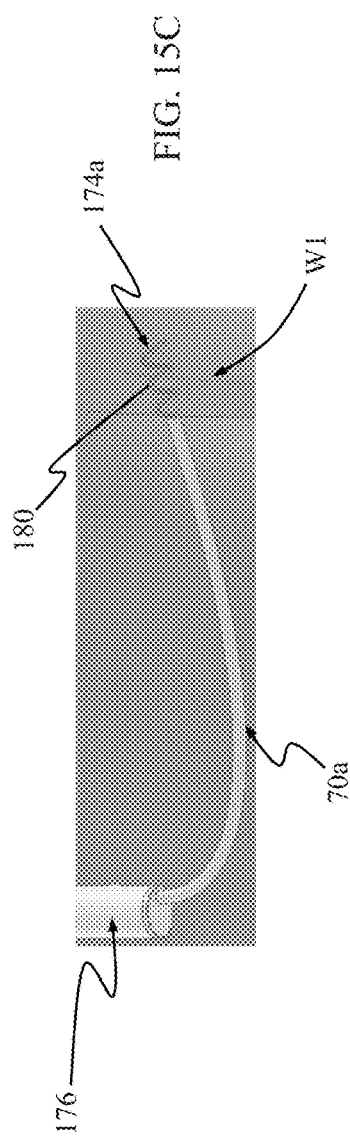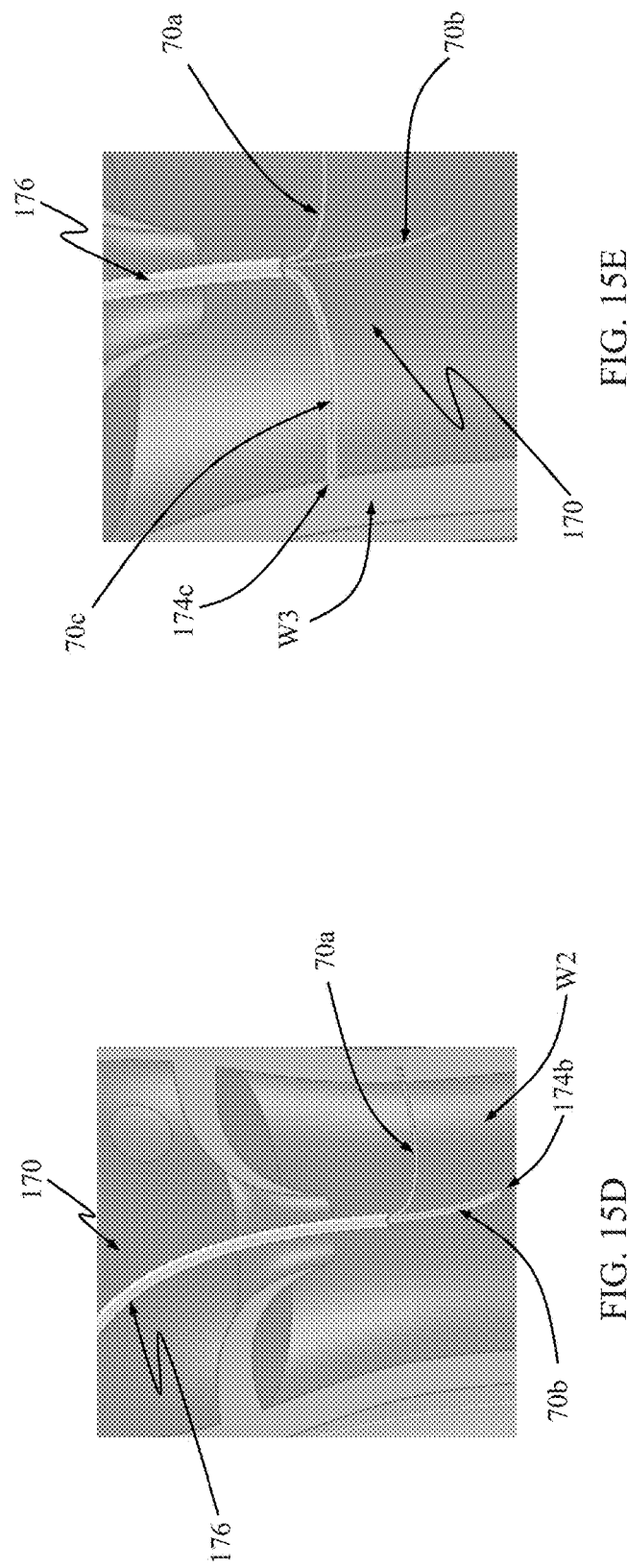
FIG. 15C
FIG. 15D
FIG. 15E

PROSTHETIC HEART VALVE DELIVERY SYSTEMS AND METHODS

CROSS REFERENCE TO RELATED APPLICATION

This Non-Provisional Patent Application claims the benefit of the filing dates of U.S. Provisional Patent Application Ser. No. 62/633,932, filed Feb. 22, 2018, the entire teachings of which are incorporated herein by reference.

BACKGROUND

The present disclosure relates to systems and methods for delivery a medical device, such as a prosthetic heart valve. More particularly, it relates to minimally invasive, transcatheter-based systems and methods for delivering a medical device, such as a prosthetic mitral valve via a transseptal approach.

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. The tricuspid valve, also known as the right atrio-ventricular valve, is a tri-leaflet valve located between the right atrium and the right ventricle. The mitral valve, also known as the bicuspid or left atrio-ventricular valve, is a bi-leaflet valve located between the left atrium and the left ventricle.

As with other valves of the heart, the mitral valve is a passive structure in that it does not itself expend any energy and does not perform any active contractile function. The mitral valve includes an annulus that provides attachment for the two leaflets (anterior leaflet and posterior leaflet) that each open and close in response to differential pressures on either side of the valve. The leaflets of the mitral valve are dissimilarly shaped. The anterior leaflet is more firmly attached to the annulus, and is somewhat stiffer than the posterior leaflet (that is otherwise attached to the more mobile posterior lateral mitral annulus). The anterior leaflet protects approximately two-thirds of the valve. The anterior leaflet takes up a larger part of the annulus and is generally considered to be "larger" than the posterior leaflet (although the posterior leaflet has a larger surface area). In a healthy mitral valve, then, the anterior and posterior leaflets are asymmetric.

Ideally, the leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of the valve prosthesis on the beating heart, intending to obviate the need for the use of classical sternotomy and cardiopulmonary bypass. In general terms, an expandable prosthetic valve is compressed about or within a catheter, inserted inside a body lumen of the patient, such as the femoral artery, and delivered to a desired location in the heart.

The heart valve prosthesis employed with catheter-based, or transcatheter, procedures generally includes an expandable frame or stent that supports a valve structure having a plurality of leaflets. The frame can be contracted during percutaneous transluminal delivery, and expanded upon deployment at or within the native valve. One type of valve stent can be initially provided in an expanded or uncrimped condition, then crimped or compressed about a balloon portion of a catheter. The balloon is subsequently inflated to expand and deploy the prosthetic heart valve. With other stented prosthetic heart valve designs, the stent frame is formed to be self-expanding. With these systems, the valved stent is crimped down to a desired size and held in that compressed state within a sheath for transluminal delivery. Retracting the sheath from this valved stent allows the stent to self-expand to a larger diameter, fixating at the native valve site. In more general terms, then, once the prosthetic valve is positioned at the treatment site, for instance within an incompetent native valve, the stent frame structure may be expanded to hold the prosthetic valve firmly in place. One example of a stented prosthetic valve is disclosed in U.S. Pat. No. 5,957,949 to Leonhardt et al., which is incorporated by reference herein in its entirety. Another type of valve stent can be initially provided in an expanded or uncrimped condition, then crimped or compressed about a balloon of a balloon catheter. The balloon is subsequently inflated to expand and deploy the prosthetic heart valve.

The actual shape and configuration of any particular transcatheter prosthetic heart valve is dependent, at least to some extent, upon the valve being replaced or repaired (i.e., mitral valve, tricuspid valve, aortic valve, or pulmonary valve). The stent frame must oftentimes provide and maintain (e.g., elevated hoop strength and resistance to radially compressive forces) a relatively complex shape in order to achieve desired fixation with the corresponding native anatomy. Moreover, the stent frame must have a robust design capable of traversing the tortuous path leading to the native valve annulus site. These design features can give rise to delivery obstacles such as difficulties in precisely locating and rotationally orienting the prosthetic valve relative to the native annulus.

Anatomical constraints can also present difficult delivery obstacles. For example, the mitral valve controls the flow of blood from the left atrium to the left ventricle. There are various minimally invasive treatments that can be done on the mitral valve and related anatomy. For example, with one procedure to gain transcatheter access to the mitral valve, the delivery device is directed through the vena cava to the right atrium, and then to the left atrium via a puncture in the atrial septum (the wall of tissue that separates the left atrium from the right atrium). This procedure to access the mitral valve from the left atrium is sometimes referred to as a transseptal approach. Regardless, once located in the left atrium, it can be difficult to manipulate the delivery system within the confines of the left atrium so as to align the prosthetic valve with the native annulus. Similar concerns are presented by other transcatheter valve delivery procedures using other approaches and/or in access other valves of the heart.

SUMMARY

The inventors of the present disclosure recognized that a need exists for transcatheter delivery devices and methods that address one or more of the above-mentioned problems.

Some aspects of the present disclosure relate to methods of delivering a prosthetic heart valve. The methods including advancing a distal region of a guide member assembly into a heart of a patient. The distal region is docked to native anatomy of the heart. A delivery device, including a collapsed prosthetic heart valve, is advanced over the docked guide member assembly. The collapsed prosthetic heart valve is located at an implantation site. The prosthetic heart valve is deployed from the delivery device, and then the delivery device is removed from the patient. At least a portion of the guide member assembly is removed from the patient. In some embodiments, the docking structure is docked to one or more of native mitral valve leaflets, chordae in the left ventricle, or walls of the left ventricle as part of a transseptal mitral valve delivery procedure.

BRIEF DESCRIPTION OF THE DRAWINGS

FIGS. 15A-15E illustrates methods of the present disclosure, including use of the guide member assembly of FIG. 14;

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. As used herein with reference to an implanted valve prosthesis, the terms "distal", "outlet", and "outflow" are understood to mean downstream to the direction of blood flow, and the terms "proximal", "inlet", or "inflow" are understood to mean upstream to the direction of blood flow. In addition, as used herein, the terms "outward" or "outwardly" refer to a position radially away from a longitudinal axis of a delivery device or a frame of the valve prosthesis and the terms "inward" or "inwardly" refer to a position radially toward a longitudinal axis of the delivery device or the frame of the valve prosthesis. As well the terms "backward" or "backwardly" refer to the relative transition from a downstream position to an upstream position and the terms "forward" or "forwardly" refer to the relative transition from an upstream position to a downstream position.

Embodiments of the present disclosure provide systems, methods, tools and devices for treating a native heart valve, such as in delivering a prosthetic heart valve. Although the description is in the context of treatment of heart valves such as the mitral valve, the systems and methods of the present disclosure also may be used in any other body passageways, organs, etc., where it is deemed useful. Further, while the systems and methods of the present disclosure can be sell-suited for transseptal approaches to the left atrium and mitral valve, features of the present disclosure can also be implemented with other surgical approaches such as retrograde aortic delivery, antegrade approaches, transapical, transatrial, etc., and combinations thereof. Furthermore, there is no intention to be bound by any expressed or implied theory presented in the present disclosure.

Figure 1:
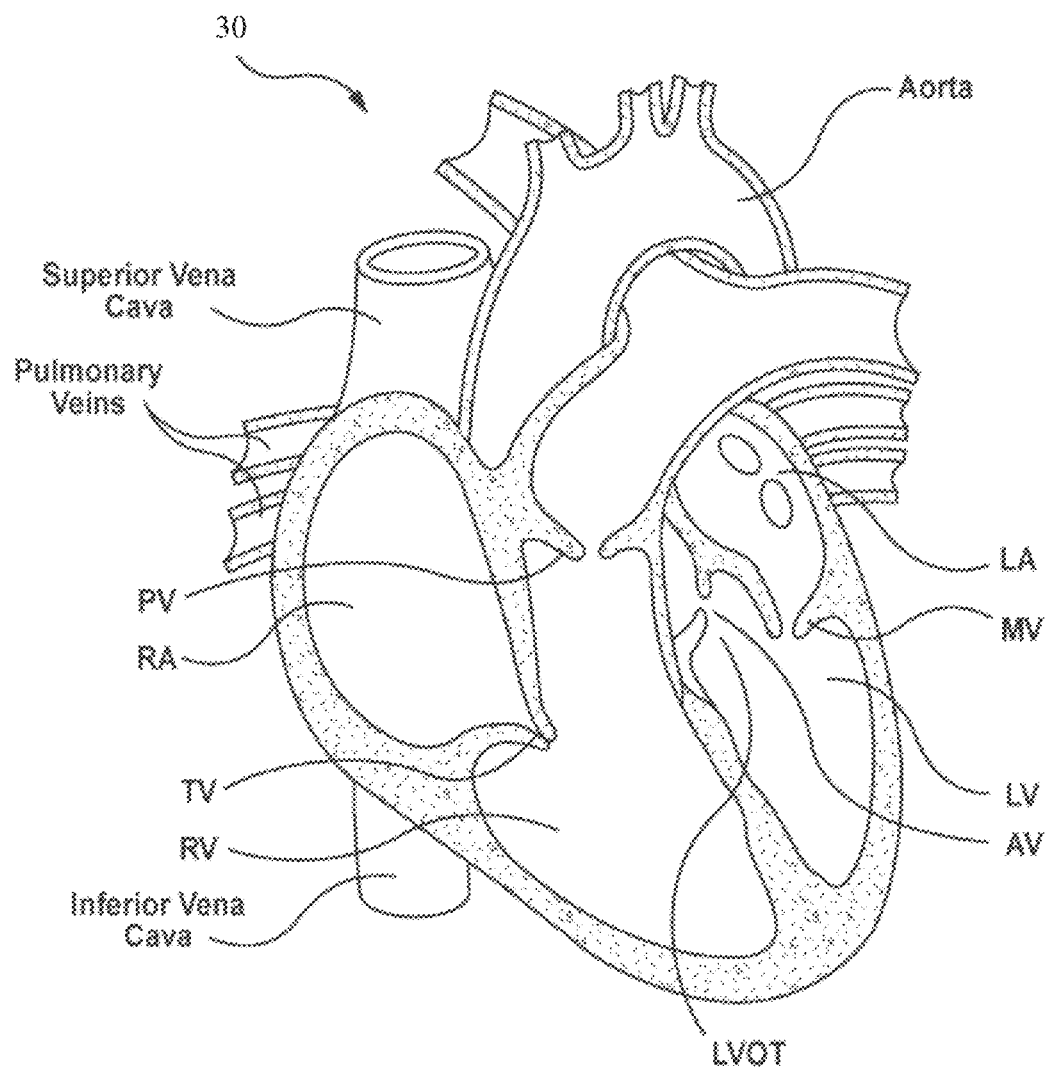
FIG. 1 is a schematic sectional illustration of a mammalian heart having native valve structures.
Figure 2:
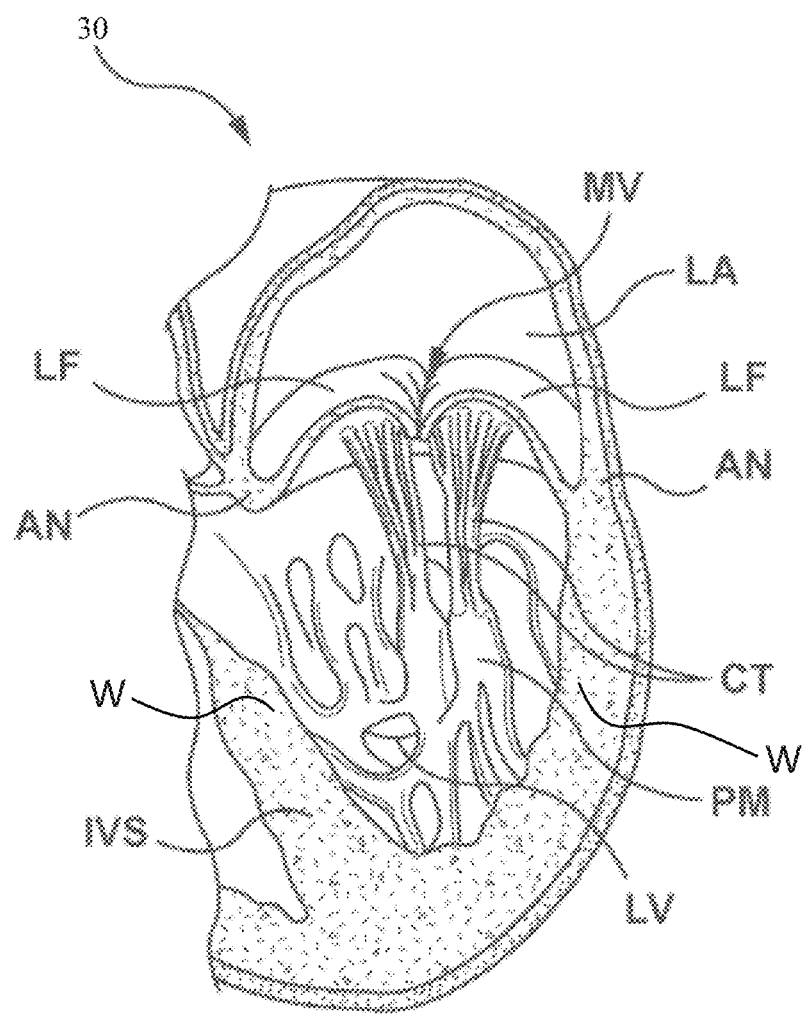
FIG. 2 is a schematic sectional illustration of a left ventricle of a mammalian heart showing anatomical structures and a native mitral valve.

By way of background, FIG. 1 is a schematic sectional illustration of a mammalian heart 30 that depicts the four heart chambers (right atria RA, right ventricle RV, left atria LA, left ventricle LV) and native valve structures (tricuspid valve TV, mitral valve MV, pulmonary valve PV, aortic valve AV). FIG. 2 is a schematic sectional illustration of a left atria LA and left ventricle LV of the heart 30 showing anatomical structures and a native mitral valve MV. Referring to FIGS. 1 and 2 together, the heart 30 comprises the left atrium LA that receives oxygenated blood from the lungs via the pulmonary veins. The left atrium LA pumps the oxygenated blood through the mitral valve MV and into the left ventricle LV during ventricular diastole. The left ventricle LV contracts during systole and blood flows outwardly through the aortic valve AV, into the aorta and to the remainder of the body.

In a healthy heart, the leaflets LF of the mitral valve MV meet evenly at the free edges or "coapt" to close and prevent back flow of blood during contraction of the left ventricle LV (FIG. 2). Referring to FIG. 2, the leaflets LF attach the surrounding heart structure via a dense fibrous ring of connective tissue called an annulus AN which is distinct from both the leaflet tissue LF as well as the adjoining muscular tissue of the heart wall. In general, the connective tissue at the annulus AN is more fibrous, tougher and stronger than leaflet tissue. The flexible leaflet tissue of the mitral leaflets LF are connected to papillary muscles PM, which extend upwardly from the walls W of the left ventricle LV and the interventricular septum IVS, via branching tendons called chordae tendinae CT.

Figure 3:
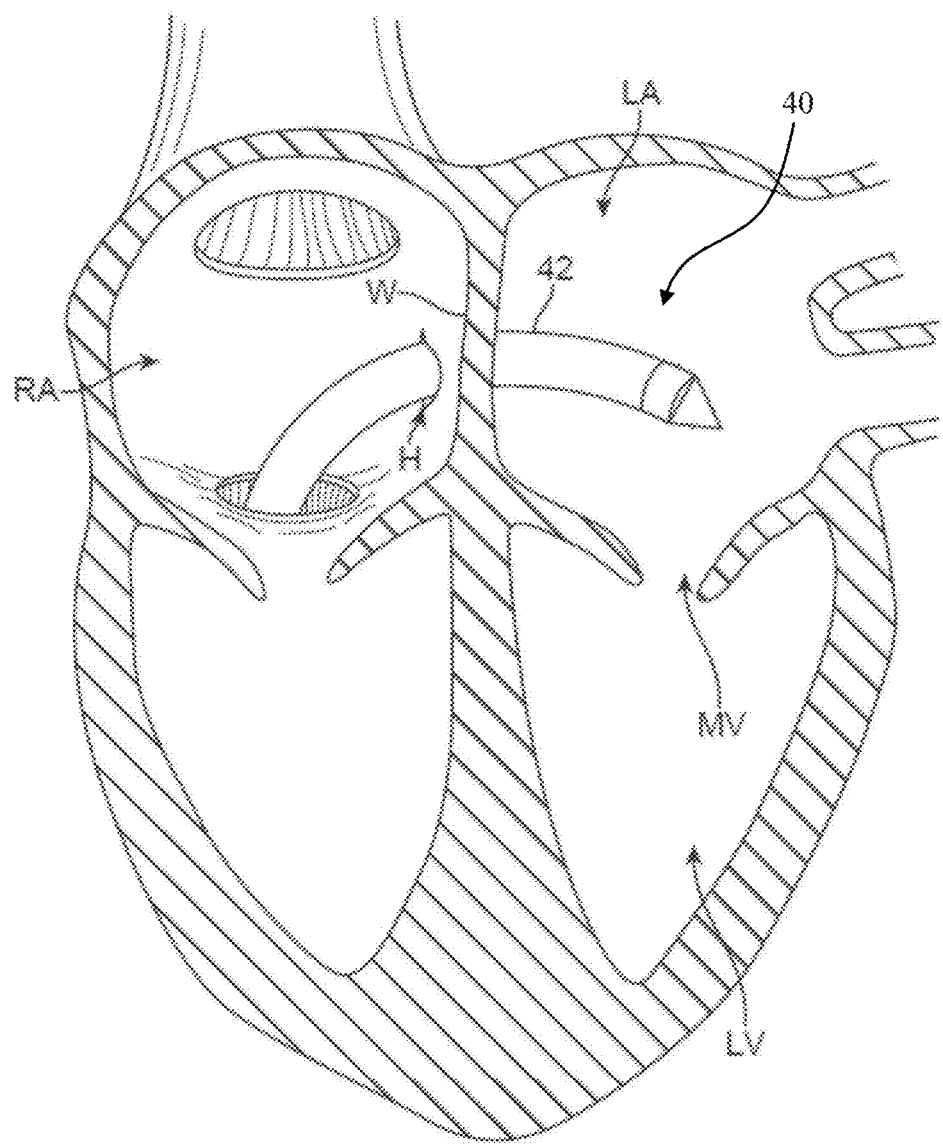
FIG. 3 is a simplified section of a human heart and illustrating a medical device having attained transseptal access of the left atrium.

One example of a treatment procedure to be performed on the heart 30 is generally reflected by FIG. 3. A transcatheter delivery device 40 is shown after having been introduced into the vasculature via a percutaneous entry point (e.g., the Seldinger technique), and having been tracked through the vasculature and into the left atrium LA. For example, the percutaneous entry point may be formed in a femoral vein. Thereafter, a guidewire or guide member (not shown) is advanced through the circulatory system, eventually arriving at the heart. The guidewire is directed into the right atrium RA (e.g., via the vena cava), traverses the right atrium RA, and is made to puncture or otherwise pass through a hole H in the atrial septal wall W (e.g., with the aid of a transseptal needle), thereby entering the left atrium LA. Once the guidewire is positioned, the delivery device 40 is tracked over the guide wire and delivered transseptally to the left atrium LA. From the arrangement of FIG. 3, the delivery device 40 is further manipulated and/or operated to perform a treatment, such as delivering and deploying a prosthetic heart valve (e.g., maintained within a capsule 42 of the delivery device 40 in the state of FIG. 3) at the mitral valve MV. In this regard, from the arrangement of FIG. 3, the delivery device 40, and in particular the capsule 42, should be caused to turn or track approximately 90 degrees downward in order to face and align with the mitral valve MV. Some embodiments of the present disclosure provide devices, tools, assemblies and methods useful with the delivery device 40 in guiding the capsule 42 (or other portion of the delivery device 40) into alignment with the mitral valve MV.

Figure 4:
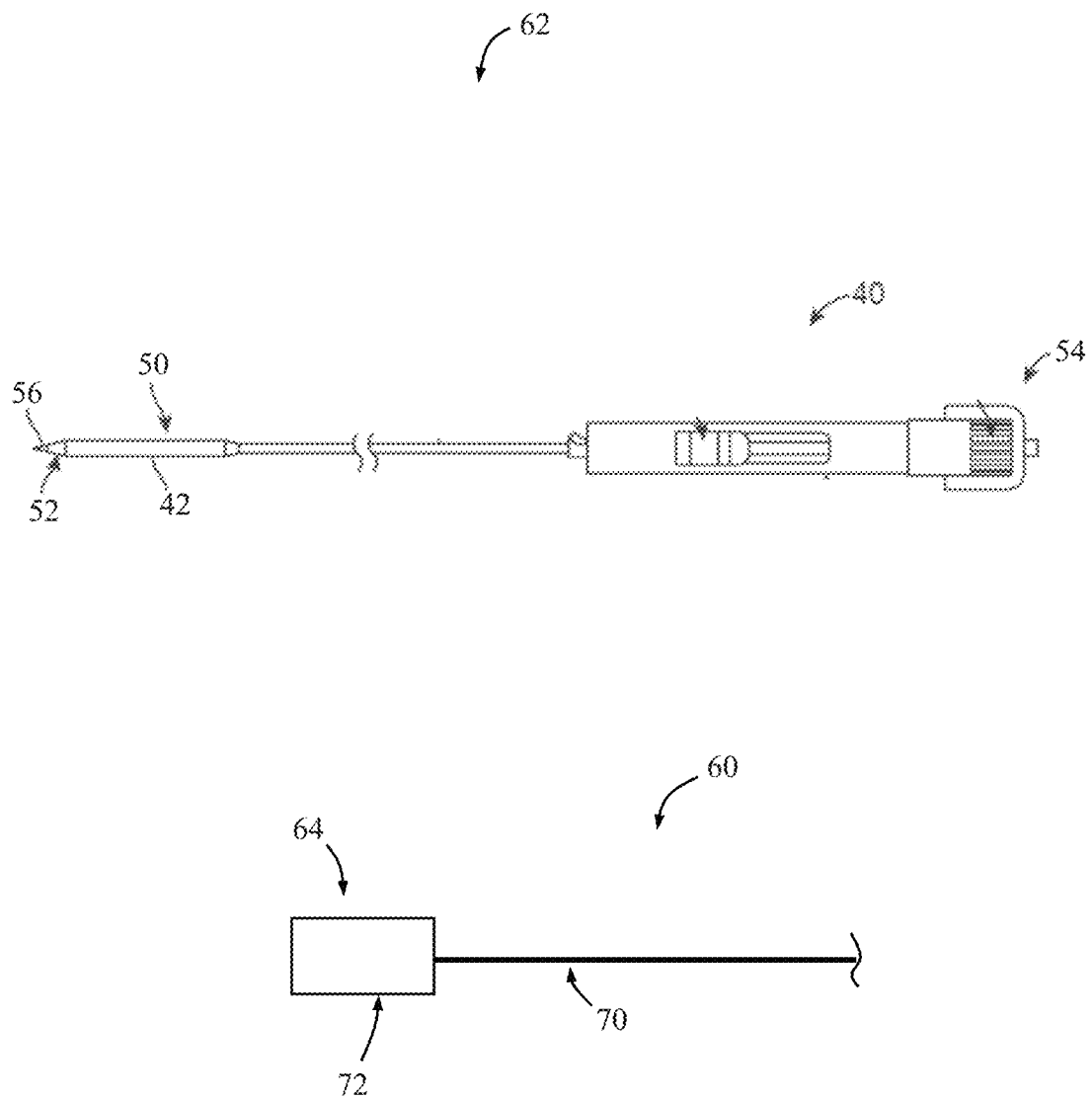
FIG. 4 is a simplified plan view of a system for transcatheter delivery of a prosthetic heart valve including a delivery device and a guide member assembly in accordance with principles of the present disclosure.

As a point of reference, the systems, devices, tools and methods of the present disclosure can be employed with a wide variety of differently-configured delivery devices. In general terms, and with reference to FIG. 4, one non-limiting embodiment of the delivery device 40 can include a delivery sheath assembly 50, a support shaft assembly 52 (referenced generally), and a handle assembly 54. The delivery device 40 provides a loaded or delivery state in which a prosthetic valve (hidden) is loaded over the support shaft assembly 52 and is retained within the capsule 42 of the delivery sheath assembly 50. The support shaft assembly 52 can include an inner shaft (hidden) connected to or terminating at a tip 56. The prosthetic valve is maintained over the inner shaft by the capsule 42. A guide member or guidewire lumen (hidden) can be provided through the tip 56 and other portions of (including an entirety of) the support shaft assembly 52, and can be open to a guide member or guidewire port (e.g., at the handle assembly 54). The delivery sheath assembly 50 can be manipulated to withdraw the capsule 42 from over the prosthetic heart valve via operation of the handle assembly 54. In some embodiments, the prosthetic heart valve may then self-expand and release from the delivery device 40. In other embodiments, the prosthetic heart valve may have a mechanically-expandable or balloon-expandable construction. For example, the delivery device 40 may include an inflatable component (e.g., a balloon) that is operated to expand the prosthetic heart valve following retraction of the capsule 42. Other delivery device constructions are also envisioned by the present disclosure, for example delivery device configurations that do not include the capsule 42.

With the above in mind, some aspects of the present disclosure relate to a guide member assembly 60 useful with the delivery device 40 as part of a prosthetic heart valve (or other medical device) delivery procedure, and corresponding methods of use. The delivery device 40 and the guide member assembly 60 combine to define a system 62 for delivering the prosthetic heart valve (or performing other transcatheter-based treatment procedures). As described below, the guide member assemblies of the present disclosure can assume a wide variety of forms, and features of some guide member assembly formats can be combined with or incorporated into other guide member assembly embodiments.

In some embodiments, the guide member assembly 60 provides a distal region 64, and includes an elongated member (or rail or guide member) 70 and a docking structure 72 (shown in block form). In some embodiments, the elongated member 70 may comprise a surgical guidewire of known or conventional construction useful in the catheter arts and appropriate for insertion into a patient. In some embodiments, the elongated member 70 exhibits sufficient flexibility for atraumatic guidance through a patient's vasculature to the heart in accordance with an intended procedure, and sufficient rigidity for tracking or guiding a transcatheter delivery device (such as the exemplary delivery device 40 of FIG. 4)) over the elongated member 70. In some embodiments, portions or an entirety of the elongated member 70 can be configured to assume a pre-determined shape (e.g., longitudinal curvature). In some embodiments, the elongated member 70 is not configured to self-assume a pre-determined shape. The elongated member 70 can be formed of metal, plastic, fibers, strands, wire, etc. (e.g., the elongated member 70 can comprise a wire or a suture).

Figure 5A:
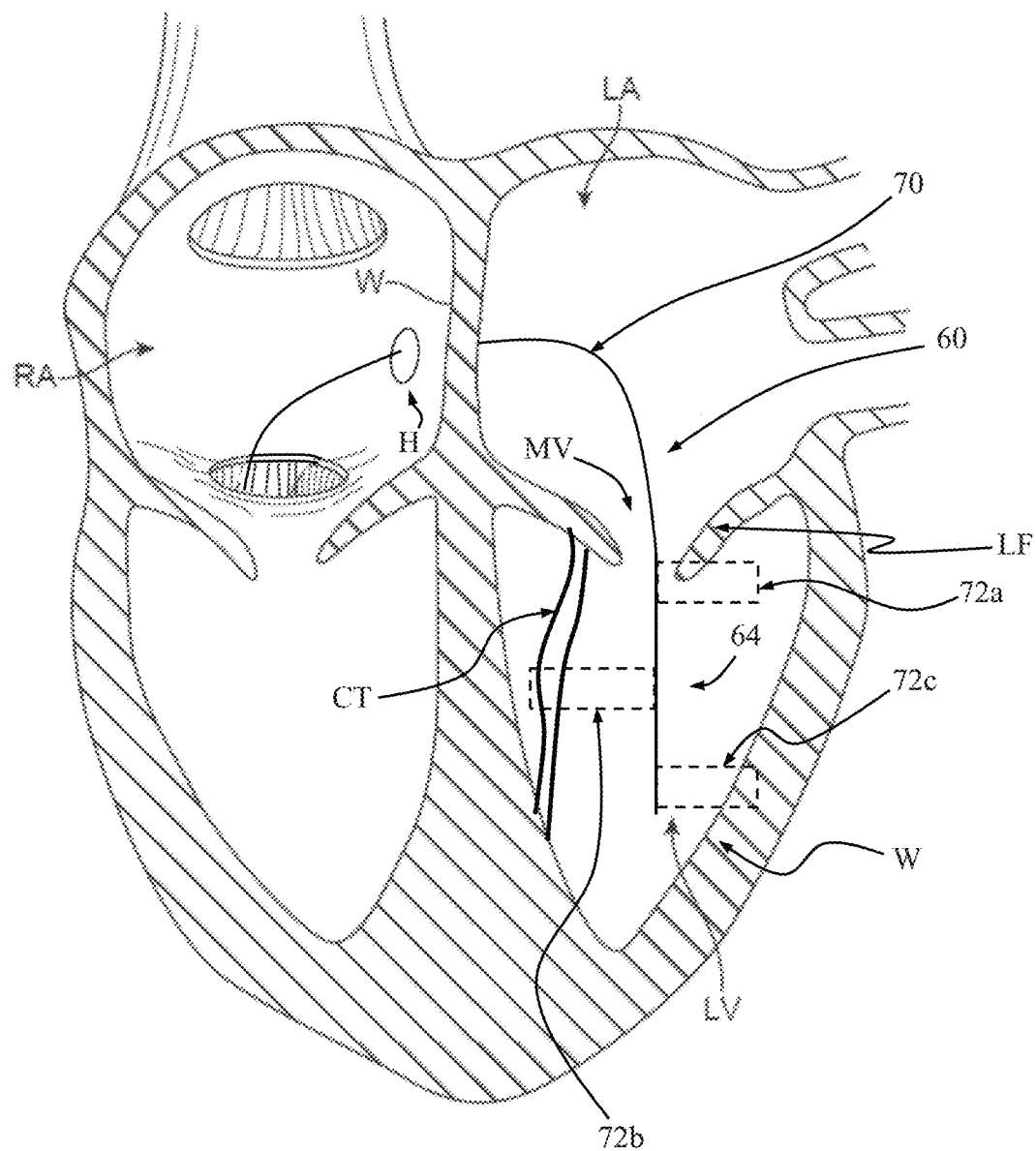
FIGS. 5A-5C illustrate methods in accordance with principles of the present disclosure.

The docking structure 72 is carried by or assembled to the elongated member 70 and is generally configured to interface or dock with expected native anatomy, for example native anatomy associated (e.g., adjacent) with the mitral valve. By way of non-limiting example and with additional reference to FIG. 5A, the docking structure 72 can be configured to interface or dock with one or more native valve leaflets LF (e.g., the docking structure shown in block form and with dashed lines at 72*a*), one or more chordae CT (e.g., the docking structure shown in block form and with dashed lines at 72*b*), one or more of the walls W (e.g., the docking structure shown in block form and with dashed lines at 72*c*) of the left ventricle LV, etc., as described in greater detail below. As a point of further reference, the view of FIG. 5A illustrates portions of some non-limiting methods of the present disclosure in which the distal region 64 of the guide member assembly 60 has attained initial crossing of the inter-atrial septum H to the left atrium LA, then crossing of the mitral valve MV. A catheter or similar device (not shown) can be used in directing the elongated member 70 to the arrangement of FIG. 5A in some embodiments. Regardless, once the docking structure 72 is engaged with native anatomy (e.g., one or more of the leaflets, chordae CT, wall(s) W of the left ventricle LV, etc.), the elongated member 70 provides a stable rail over which a larger diameter system or device can be tracked or guided over, and, in some embodiments, eliminating the need for active steering of the larger system.

Figure 5B:
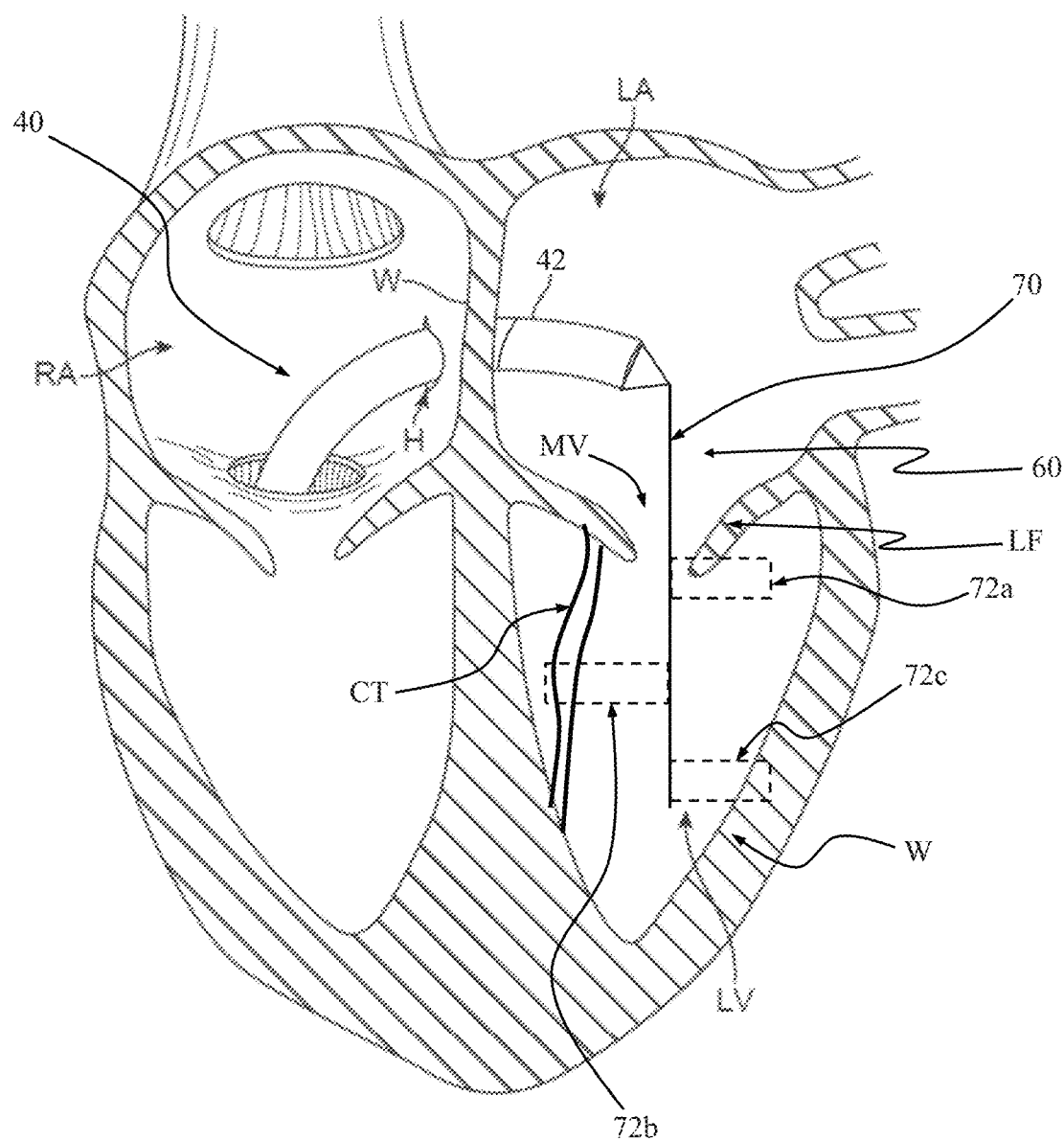
Figure 5C:
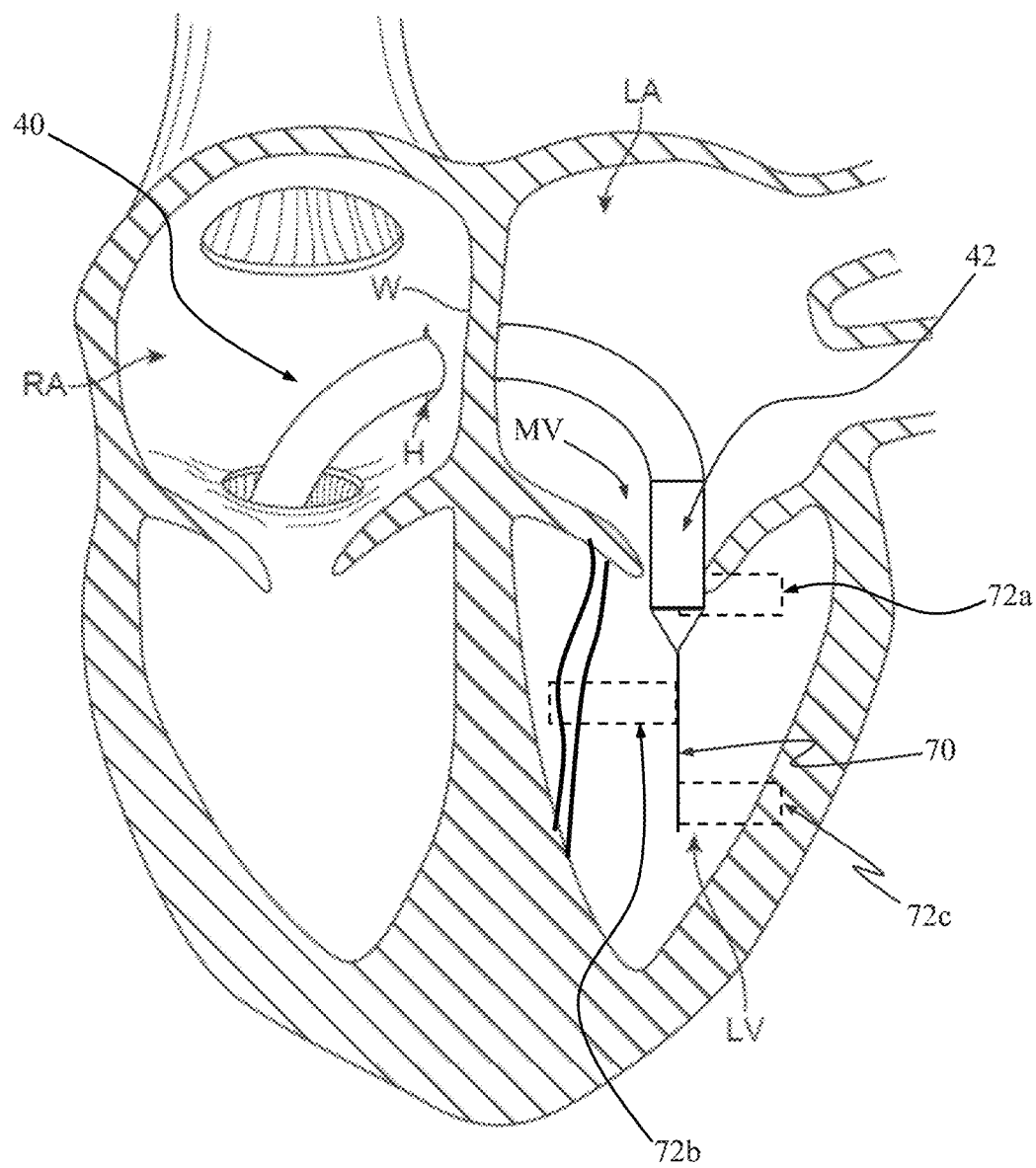

For example, in the view of FIG. 5B, the delivery device 40 carrying a collapsed prosthetic mitral valve (hidden within the capsule 42) has been directed to the left atrium LA via a transseptal approach as described above. The guide member assembly 60 can be utilized in initially directing the delivery device 40 to the arrangement of FIG. 5B. In some embodiments, the guide member assembly 60 can be manipulated, steered or advanced into the left atrium LA or left ventricle LV. In some embodiments, the guide member assembly 60 can be directed into the left atrium LA or left ventricle LV via a conventional guidewire. In some embodiments, a conventional guidewire can be employed to locate the delivery device 40 in the left atrium LA (e.g., to the arrangement of FIG. 5B), and then the guidewire can be replaced with the guide member assembly 60 (e.g., the guidewire is removed). Regardless, before, after or simultaneous with locating the capsule 42 within the left atrium LA, the distal region 64 of the guide member assembly 60 is manipulated, steered and/or advanced as described above, directing the docking structure 72 through and beyond the mitral valve MV. The guide member assembly 60 is then manipulated to dock the docking structure 72 to native anatomy. From the state of FIG. 5B, the delivery device 40 is then advanced over the elongated member 70, bringing the capsule 42 into the mitral valve MV as in FIG. 5C. Because the docking structure 72 is relatively fixed to the native anatomy, a push/pull tension can be applied to the elongated member 70 allowing the delivery device 40 to be more readily distally advanced over the elongated member 70. Further, because the elongated member 70 remains generally aligned with the mitral valve MV via the docked docking structure 72, the capsule 42 will be similarly directed into and aligned with the mitral valve MV. The delivery device 40 is then operated to deploy the prosthetic heart valve.

Various examples of docking structures 72 in accordance with principles of the present disclosure are provided below. In some embodiments, the docking structure 72 can be configured to transition (e.g., expand and collapse) between a delivery arrangement and a deployed or capture arrangement or state. In some embodiments, the docking structure 72 can be selectively detachable from the elongated member 70. Portions or an entirety of the docking structures of the present disclosure can be made from stainless steel, a pseudo-elastic metal such as a nickel titanium alloy or Nitinol™, or a so-called super alloy, which may have a base metal of nickel, cobalt, chromium, or other metal. In yet other embodiments, any of the docking structures of the present disclosure can alternatively be provided as part of the delivery device 40, e.g., tip or nosecone 56 (FIG. 4), with the so-configured tip 56 being advanced via the elongated member 70 to engage native anatomy as described below.

Figure 6A:
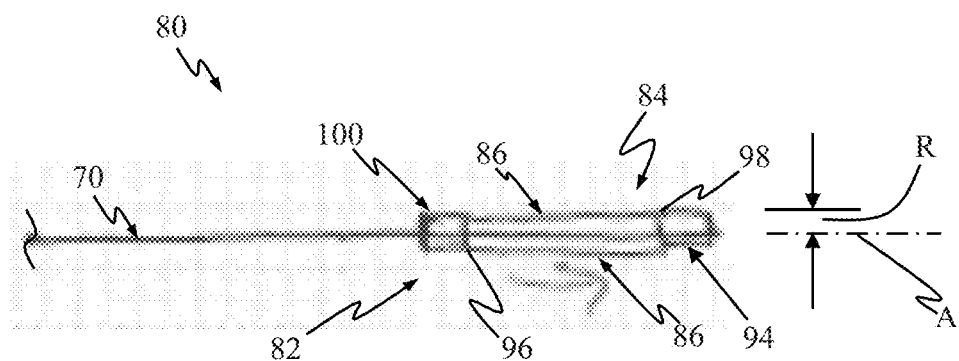
FIG. 6A is a simplified side view of guide member assembly in accordance with principles of the present disclosure and useful with the systems and methods of the present disclosure, the assembly including a docking structure in a delivery arrangement.
Figure 6B:
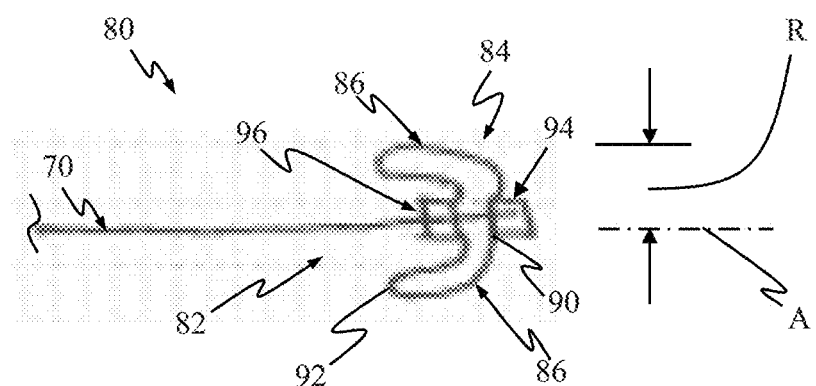
FIG. 6B is a simplified side view of the guide member assembly of FIG. 6A, illustrating the docking structure in a capture arrangement.

With the above explanations in mind, portions of one embodiment of a guide member assembly 80 in accordance with principles of the present disclosure and useful as the guide member assembly 60 (FIG. 4) provided with the systems 62 (FIG. 4) of the present disclosure is shown in simplified form in FIGS. 6A and 6B. The guide member assembly 80 provides a distal region 82, and includes the elongated member 70 as described above and a docking structure 84. The docking structure 84 is carried by or assembled to the elongated member 70 and is generally configured to interface or dock with expected anatomy. For example, with the construction of FIGS. 6A and 6B, the docking structure 84 includes at least one anchor member or arm 86 configured to selectively interface with a native valve leaflet(s), such as native mitral valve leaflets. In some embodiments, the docking structure 84 is configured such that the anchor member(s) 86 is collapsible, for example being transitionable between a delivery arrangement (FIG. 6A) and a deployed or capture arrangement (FIG. 6B). In the delivery arrangement, the anchor member(s) 86 has a streamlined shape, with at least majority, optionally an entirety, of the anchor member(s) 86 being in close proximity to the elongated member 70. In the deployed or capture arrangement, at least a portion of the anchor member(s) 86 projects radially from the elongated member 70 to define a capture region. Stated otherwise, each of the anchor members 86 has a maximum radial dimension R relative to a longitudinal axis A defined by the elongated member 70; the maximum radial dimension R in the capture arrangement (FIG. 6B) is greater than the maximal radial dimension R in the delivery arrangement (FIG. 6A). In some embodiments, the capture arrangement includes the anchor member(s) 86 assuming or reverting to a curved shape in extension from the elongated member 70 as generally reflected by FIG. 6B. In other embodiments, the anchor member(s) 86 can have a more linear or planar shape in projection from the elongated member 70 in the capture arrangement. Regardless, in some embodiments, the capture arrangement can include the anchor member(s) 86 projecting from the elongated member 70 in a generally proximal direction. For example, the anchor member(s) 86 can, in the capture arrangement, be viewed as defining or providing a base 90 and a tip 92. The base 90 is most proximate the elongated member 70, and effectively represents a point of departure of the anchor member 86 from the elongated member 70. The tip 92 is defined opposite the base 90, and can correspond to the maximal radial dimension R. With these definitions in mind, proximal projection of the anchor member 86 from the elongated member 70 in the proximal direction can include the tip 92 being proximal the base 90 (and radially spaced from the elongated member 70).

The optional collapsible configuration of the anchor member(s) 86 can be provided in various fashions. In some non-limiting embodiments, the docking structure 84 can further include first and second rings 94, 96. As identified in FIG. 6A, a first end 98 of each of the anchor members 86 is attached to the first ring 94, and an opposing second end 100 is attached to the second ring 96. The first ring 94 is fixedly mounted to the elongated member 70, whereas the second ring 96 is slidably mounted over the elongated member 70 proximal the first ring 94. During use, transitioning of the docking structure 84 includes the second ring 96 sliding along the elongated member 70 in the distal direction toward the first ring 94, with the anchor member(s) 86 deflecting (or being caused to deflect) to the capture arrangement, including the tip 92 being located at a radial spacing from the elongated member 70. A reverse action can be performed in transitioning of the anchor member(s) 86 from the capture arrangement to the delivery arrangement. In some embodiments, the guide member assembly 80 can further include one or more components or mechanisms by which a user can effect movement of the first ring 94 (e.g., a push/pull wire). In other embodiments, the anchor member(s) 86 can be configured to self-assume the capture arrangement (e.g., formed of a shape memory metal or similar material), and the guide member assembly 80 can further include an outer sheath or similar component that is slidably arranged over one or more portions of the elongated member 70 and slidably arranged over one or more portions of the anchor member(s) 86 in the delivery arrangement. With this optional construction, once removed from the confines of the outer sheath, the anchor member(s) 86 self-revert to the capture arrangement. Other configurations can be employed with the guide member assembly 80 to provide for collapsing of the anchor member(s) 86 that may or may not include the slidable ring 96. In other embodiments, the docking structure 84 is not collapsible.

Figure 7A:
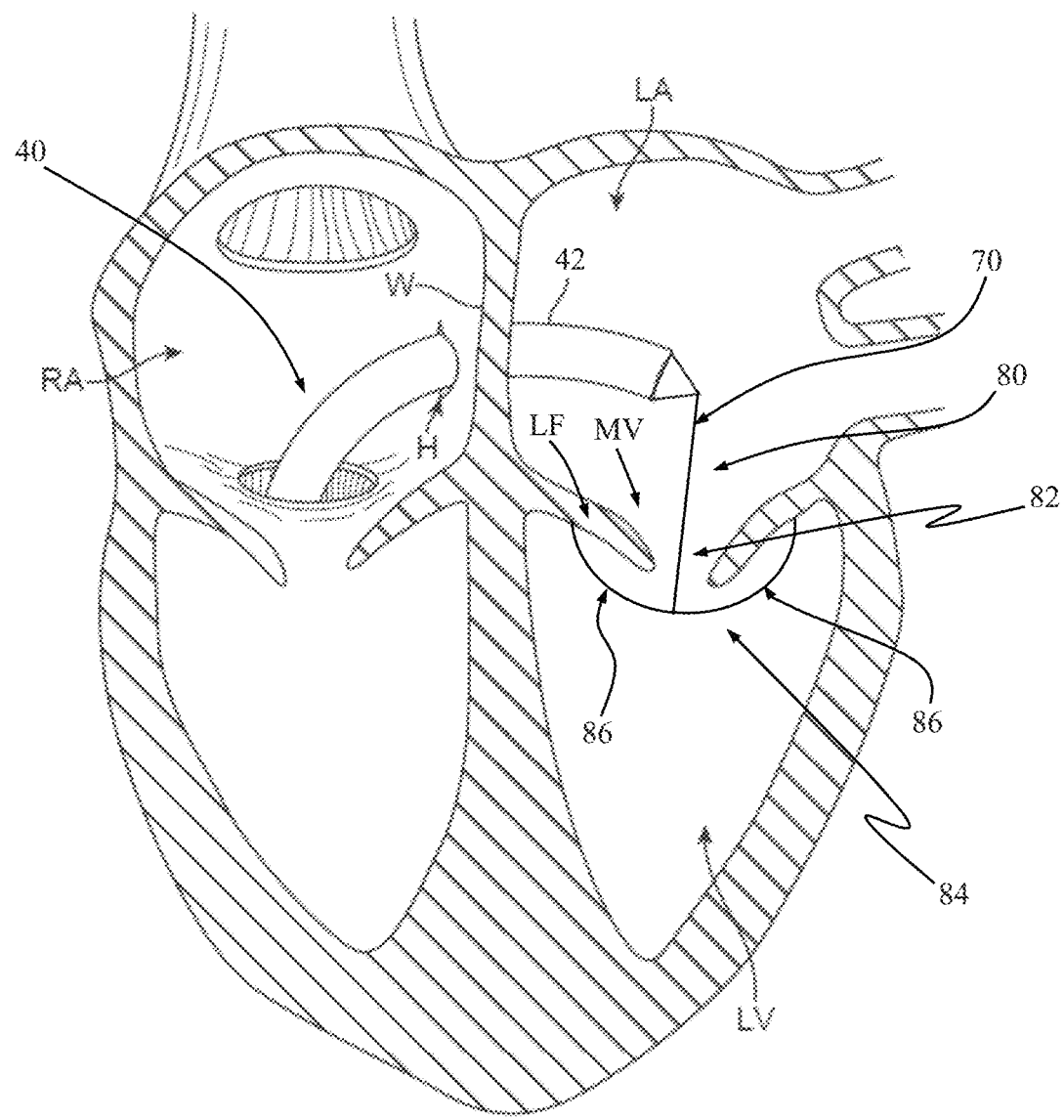
FIGS. 7A-7C illustrates methods of the present disclosure, including use of the guide member assembly of FIG. 6A.

The guide member assembly 80 can be used in connection with a number of surgical procedures, such as in connection with the transcatheter delivery of a prosthetic heart valve, for example a prosthetic mitral valve as described above. With reference to FIG. 7A, before, after or simultaneous with locating the capsule 42 within the left atrium LA, the distal region 82 of the guide member assembly 80 is manipulated, steered, and/or advanced into the heart. The distal region 82 is then further manipulated to advance the docking structure 84 through and beyond the mitral valve MV. With embodiments in which the docking structure 84 provides for a delivery arrangement and a capture or deployed arrangement, the docking structure 84 can be in the delivery arrangement when being directed through the mitral valve MV, and then transitioned to the capture or deployed arrangement. The guide member assembly 80 is then manipulated to dock the docking structure 84 to one or more of the leaflets LF. For example, with the docking structure 84 in the capture arrangement, the elongated member 70 can be distally retracted, causing the anchor member(s) 86 to capture or engage with one or more of the leaflets LF, resulting in the arrangement of FIG. 7A. The anchor member(s) 86 can include features that grab or pinch the leaflet(s) of the mitral valve MV.

Figure 7B:
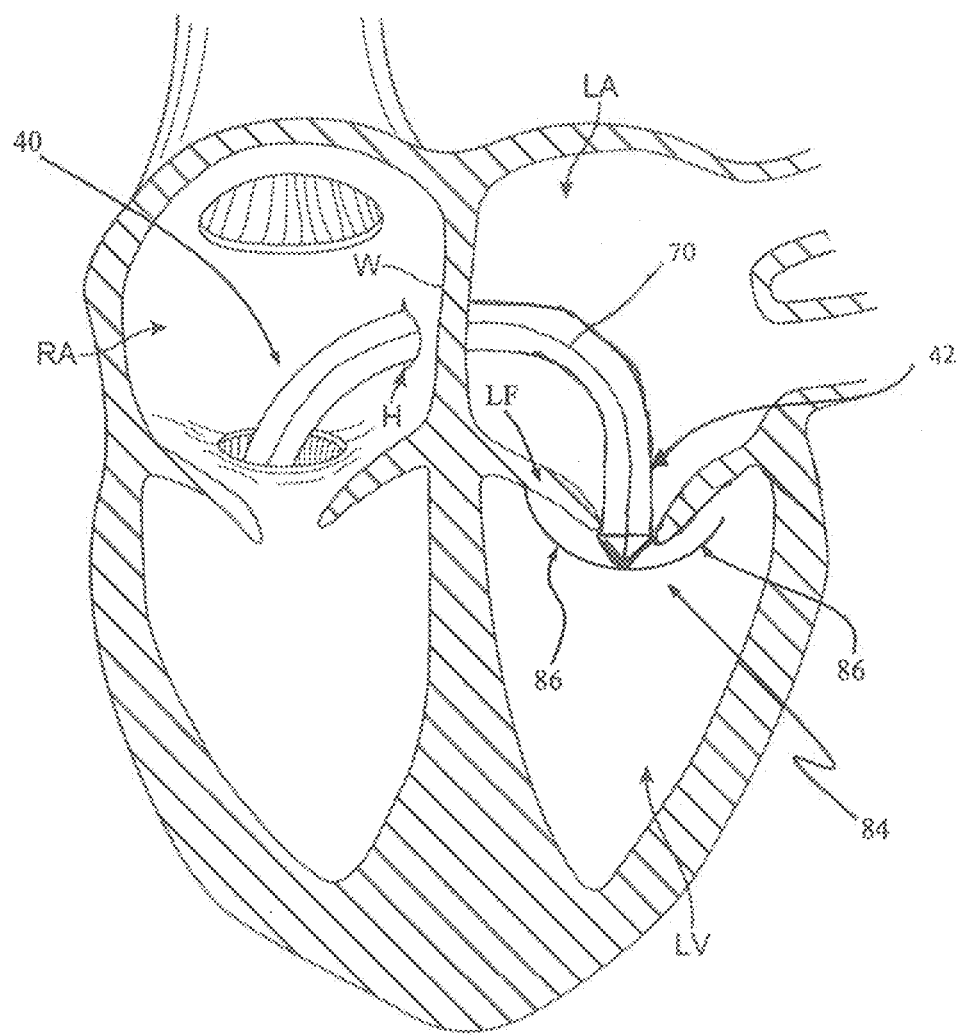
Figure 7C:
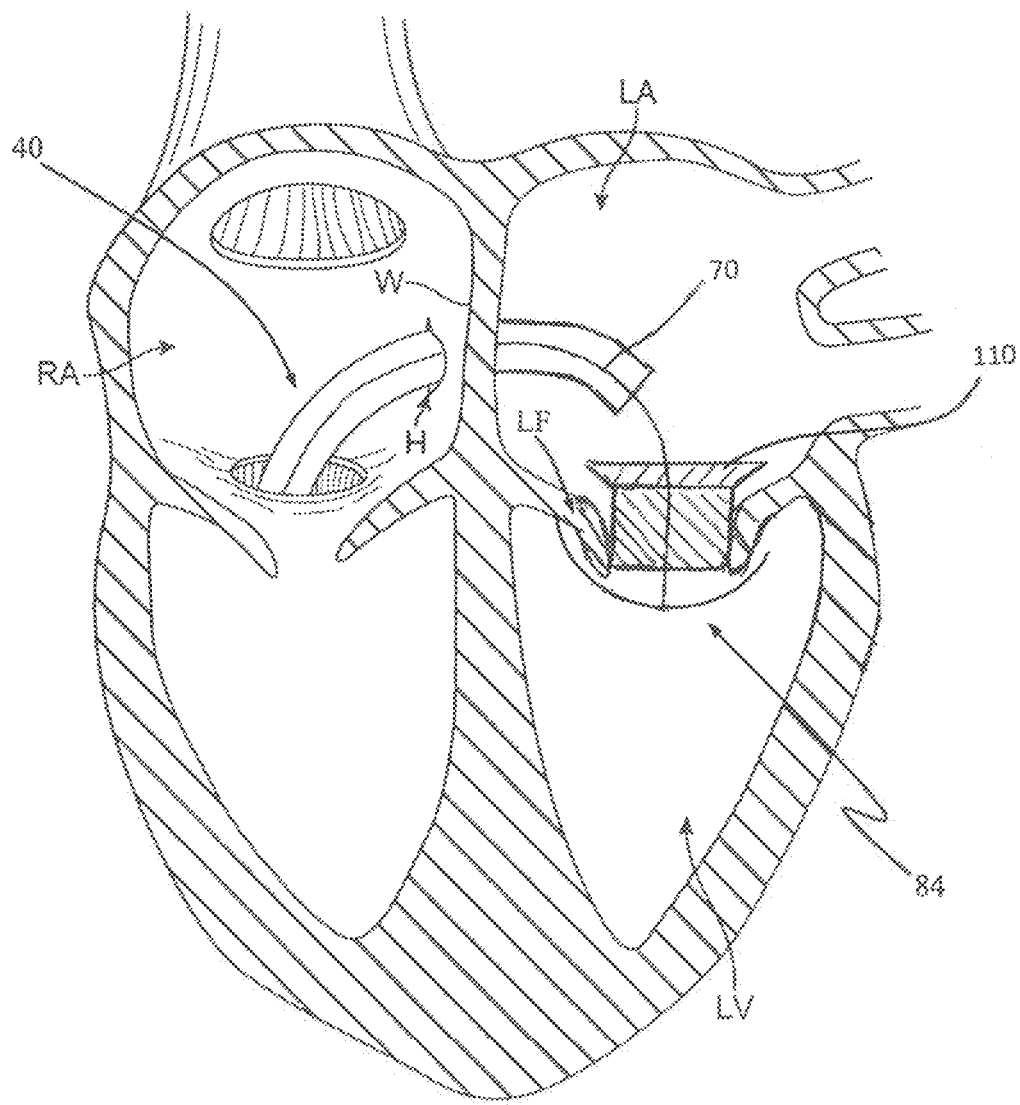

The delivery device 40 is then advanced over the elongated member 70 of the docked guide member assembly 80, bringing the capsule 42 (and the collapsed prosthetic valve within the capsule 42) into the mitral valve MV as in FIG. 7B. The delivery device 40 is then operated to deploy the prosthetic heart valve 110 as shown in FIG. 7C. For example, the capsule 42 can be retracted from over the prosthetic heart valve 110, permitting the prosthetic heart valve 110 to self-expand or otherwise deploy from the delivery device 40. Following deployment or implantation of the prosthetic heart valve 110, at least a portion of the guidewire assembly 80 is removed from the patient. For example, in some embodiments, the docking structure 84 is released from the leaflet(s) LF by distally advancing the elongated member 70, followed by transitioning of the docking structure 84 back to the delivery arrangement (FIG. 7A). The entire guide member assembly 80 can then be withdrawn from the patient.

Other surgical procedures can be facilitated using the guide member assembly 80, and the methods of the present disclosure are not limited to delivering a prosthetic heart valve. Further, other methods of the present disclosure can include temporarily or permanently docking the docking structure 84 to other native anatomical features, and are not limited to native valve leaflets LF. For example, and with additional reference to FIG. 5A, the docking structure 84 can be docked to chordae CT, cardiac wall(s) W, etc.

The docking structures of the present disclosure can assume a wide variety of other forms configured, for example, to promote docking with or within the chordae CT. For example, portions of another embodiment guide member assembly 120 are shown in simplified form in FIG. 8. The guide member assembly 120 includes the elongated member 70 as described above along with a docking structure 124. With the embodiment of FIG. 8, the docking structure 124 includes an inflatable anchor member 126, such as a balloon. An inflation medium can be supplied to an interior of the inflatable anchor member 126 via a lumen formed by the elongated member 70, or by tubing (not shown) carried by the elongated member 70. Regardless, the docking structure 124 is transitionable between the capture or deployed arrangement of FIG. 8 in which the inflatable anchor member 126 has been inflated, and a delivery arrangement in which the inflation medium has been evacuated from the inflatable anchor member 126, causing the inflatable anchor member 126 to collapse onto the elongated member 70. As part of the methods described above, and with additional reference to FIGS. 5A and 5B, the docking structure 124 (deflated or in the delivery arrangement) is advanced into the chordae CT (FIG. 5A). The inflatable anchor member 126 is then inflated (e.g., transitioned to the capture arrangement) so as to become caught up in or otherwise captured at the chordae CT. This is further reflected by FIG. 9. With continued reference to FIGS. 5A, 5B and 8, the delivery device 40 can then be advanced over the elongated member 70 to a desired location, for example locating a collapsed prosthetic heart valve (within the capsule 42) at the native mitral valve MV. Following deployment or implantation of the prosthetic heart valve, at least a portion of the guide member assembly 120 is removed from the patient. For example, in some embodiments, the docking structure 124 is released from the chordae CT by deflating the inflatable anchor member 126, by causing the inflatable anchor member 126 to burst, etc. The entire guide member assembly 120 can then be withdrawn from the patient.

In other embodiments, the docking structures and corresponding methods of use are configured for docking in a cardiac wall W, such as one or more walls W of the left ventricle LV as part of a transcatheter prosthetic mitral valve delivery procedure. The docking structures can include one or more anchor members such as screws, hooks, barbs, pincers, etc., appropriate for engaging or embedding into cardiac wall tissue. The docking structure and corresponding method of use can include docking in the apex of the left ventricle LV or side walls W of the heart depending upon alignment. The docking structure and corresponding methods of use can include a portion of the docking structure being disconnected from the elongated member 70 and remaining in situ (e.g., in the left ventricle wall W), or can be removed following the procedure (e.g., implantation of the prosthetic heart valve).

Figure 10A:
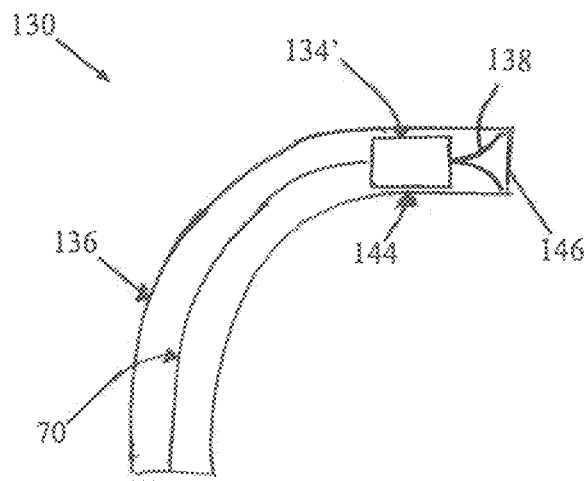
FIGS. 10A and 10B are simplified side views of another guide member assembly in accordance with principles of the present disclosure and useful with the systems and methods of the present disclosure.
Figure 10B:
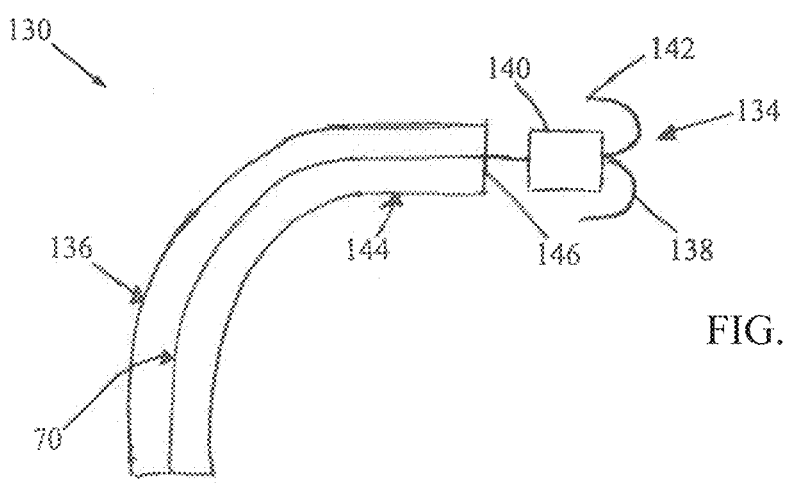

For example, another embodiment guide member assembly 130 in accordance with principles of the present disclosure is shown in FIGS. 10A and 10B, and includes the elongated member 70 as described above along with a docking structure 134 and an outer sheath or jacket 136. The docking structure 134 is transitionable between a delivery arrangement (labeled as 134' in FIG. 10A) and a capture or deployed arrangement as shown in FIG. 10B, and includes one or more anchor members 138, such as barbs, clips or other anchor members, extending from a base 140 and terminating at a tip 142 configured to pierce tissue. In some embodiments, the anchor members 138 are configured (e.g., shape memory material) or biased to the capture or deployed arrangement. The base 140 is connected to the elongated member 70 (permanently attached, releasably attached, etc.). The outer sheath 136 is slidably disposed over the elongated member 70 and forms a capsule 144 terminating at a distal end 146. The capsule 144 is configured (e.g., size, shape, hoop strength, etc.) to force and restrain the docking structure 134, and in particular the anchor members 138, to the delivery arrangement when disposed over the docking structure 134. One or both of the elongated member 70 and/or the outer sheath 136 can be provided with steering features.

Figure 11:
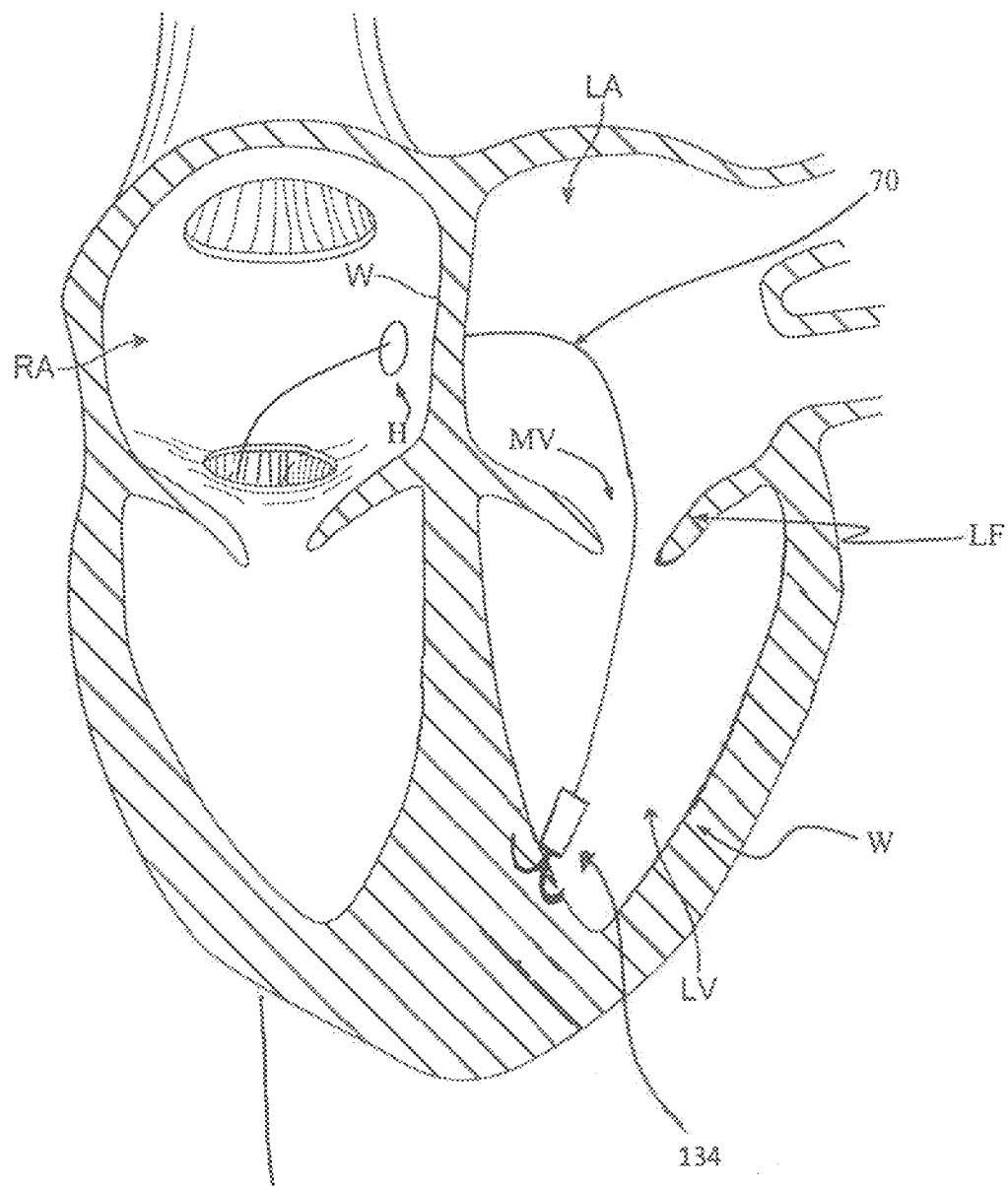
FIG. 11 illustrates methods of the present disclosure, including use of the guide member assembly of FIGS. 10A and 10B.

Some methods of the present disclosure making use of the guide member assembly 130 can include directing the guide member assembly 130, in the delivery arrangement, to the left ventricle LV (FIG. 5A) commensurate with the above explanations. The distal end 146 of the outer sheath 136 is located against the native anatomy structure of interest (e.g., a wall of the left ventricle LV). The docking structure 134 is then advanced relative to the capsule 144, with the tip 142 of each of the anchor members 138 moving distally beyond the distal end 146 and piercing into tissue. With further distal movement of the docking structure 134 and/or proximal retraction of the capsule 144, the docking structure 134 self-transitions to the capture or deployed arrangement, with the anchor members 138 embedding into the native anatomy. The outer sheath 136 can then be withdrawn, as shown for example in FIG. 11, with the docking structure 134 remaining docked to or embedded within tissue of the wall W of the left ventricle LV. A delivery device (such as the delivery device 40 (FIG. 5B)) can then be tracked or advanced over the elongated member 70 of the now-docked guide member assembly 130, followed by deployment of the prosthetic heart valve as described above. Once the procedure is complete, the outer sheath 136 (FIG. 10A) can be distally advanced over the elongated member 70, bringing the capsule 144 into close proximity with the docking structure 134. With further distal advancement of the capsule 144 and/or proximal retraction of the docking structure 134, the docking structure 134 releases from engagement with the native anatomy and returns to the delivery arrangement within the capsule 144. The guide member assembly 130 can then be withdrawn from the patient. In some embodiments, the outer sheath 136 is not withdrawn prior to placement of the delivery device (e.g., the delivery device 40 (FIG. 5B)) such that the delivery device is advanced over the outer sheath 136 of the guide member assembly 130.

Figure 12:
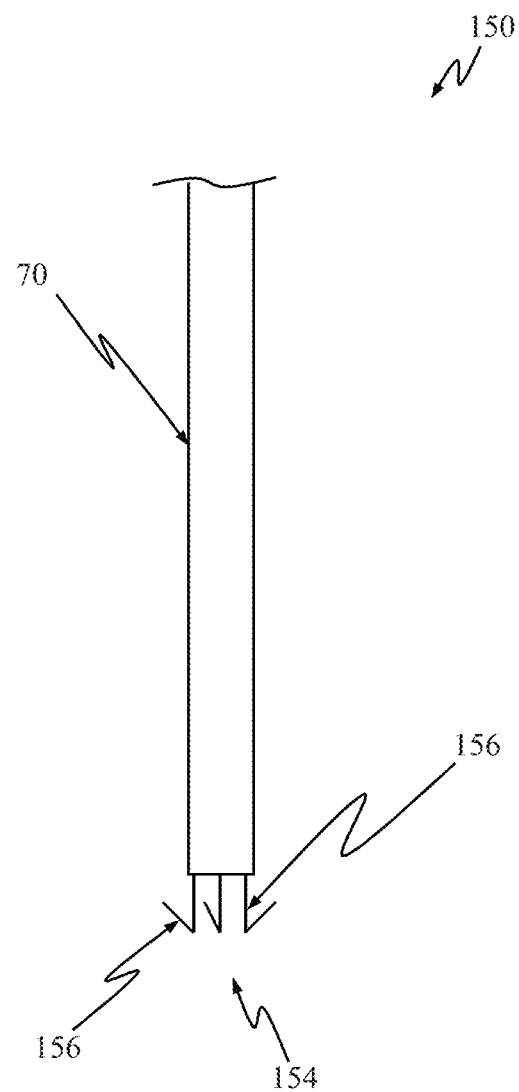
FIG. 12 is a simplified side view of another guide member assembly in accordance with principles of the present disclosure and useful with the systems and methods of the present disclosure.

Another embodiment guide member assembly 150 in accordance with principles of the present disclosure is shown in FIG. 12, and includes the elongated member 70 as described above along with a docking structure 154. The docking structure 154 is or includes two or more clips or anchor members 156 each carried within a lumen or lumens (not shown) of the elongated member 70. The anchor members 156 are biased to assume the capture or deployed arrangement depicted in FIG. 12, and can be retracted within the corresponding lumen of the elongated member 70, bending to a straightened shape to provide a delivery arrangement. In some embodiments, the docking structure 154, and optionally the elongated member 70, incorporate clip retraction and deployment features and technology embodied by a miniature transcatheter pacing system available under the trade designation MICRA™ from Medtronic, Inc. Some methods of the present disclosure making use of the guide member assembly 150 can be highly akin to the methods above with respect to the guide member assembly 130 (FIG. 10) in which the docking structure 154 is transitioned to the capture or deployed arrangement, engaging tissue (e.g., cardiac wall (FIG. 5A)) and docking the elongated member 70 relative to the native anatomy.

Figure 13:
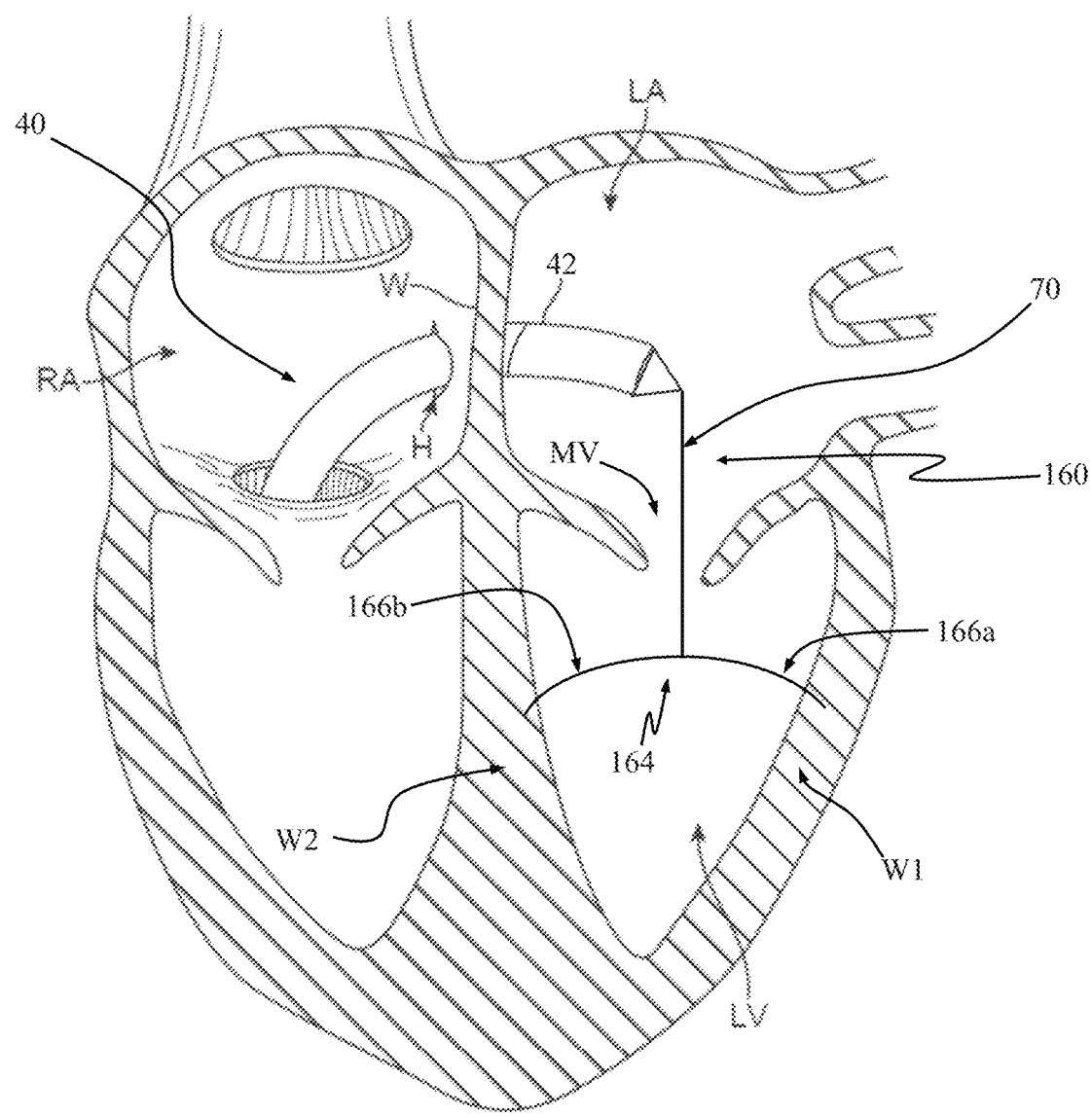
FIG. 13 is a simplified side view of another guide member assembly in accordance with principles of the present disclosure and in performing methods of the present disclosure.

Another embodiment guide member assembly 160 in accordance with principles of the present disclosure is shown in FIG. 13, and includes the elongated member 70 as described above along with a docking structure 164. The docking structure 164 is attached to or carried by the elongated member 70 and provides the capture arrangement as shown in which the docking structure 164 spans the left ventricle LV and docks or engages opposing wall sections W1, W2 of the left ventricle LV. For example, the docking structure 134 can included two or more anchor members, such as anchor members 166*a*, 166*b*, that project generally radially in differing directions from the elongated member 70; when brought into anchoring contact with wall sections W1, W2, the anchor members 166*a*, 166*b* serve to generally center the elongated member 70 relative to the left ventricle LV (and thus generally center the elongated member 70 relative to the mitral valve MV). The anchor members 166*a*, 166*b* can self-deploy (e.g., shape memory metal) to the capture or deployed arrangement from a delivery arrangement in some embodiments. Regardless, the guide member assembly 160 can be used with methods of the present disclosure commensurate with the descriptions above.

Figure 14:
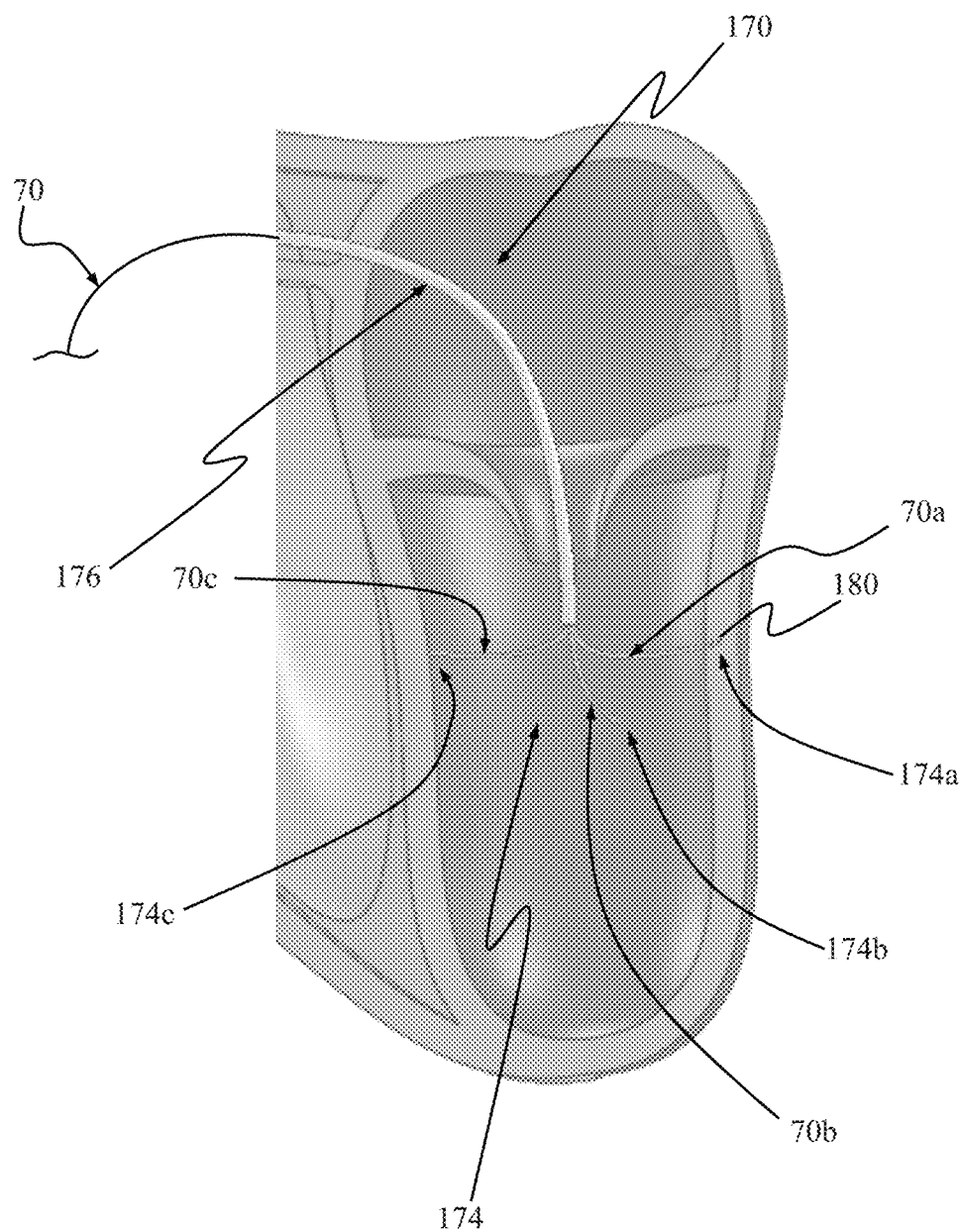
FIG. 14 is a simplified perspective view of another guide member assembly in accordance with principles of the present disclosure and in performing methods of the present disclosure.

Portions of another embodiment guide member assembly 170 in accordance with principles of the present disclosure are shown in FIG. 14, and includes one or more of the elongated members 70 as described above along with one or more docking structures 174 and an outer sheath or jacket 176. In one embodiment, and as shown in FIG. 14, the guide member assembly 170 includes three elongated members 70*a*, 70*b*, 70*c*, each terminating at or carrying a docking structure 174*a*, 174*b*, 174*c* that includes an anchor member 180 (e.g., a screw, barb, etc.). The elongated member 70*a*, 70*b*, 70*c* are slidably disposed along or within corresponding lumens of the outer sheath 176. The guide member assembly 170 can further include one or more steering wires (not shown) connected to the outer sheath 176 and operable to manipulate or steer the outer sheath 176 as described in greater detail below. The outer sheath 176 can be a polymer or co-polymer material, such as medical-grade thermoplastic polyurethane elastomers. The elongated members 70*a*, 70*b*, 70*c* can be made of a rigid material such as stainless steel, nitinol, PTFE, etc. The anchor members 180 (e.g., screws) can be formed as a stainless steel or nitinol coil, etc.

Figure 15A:
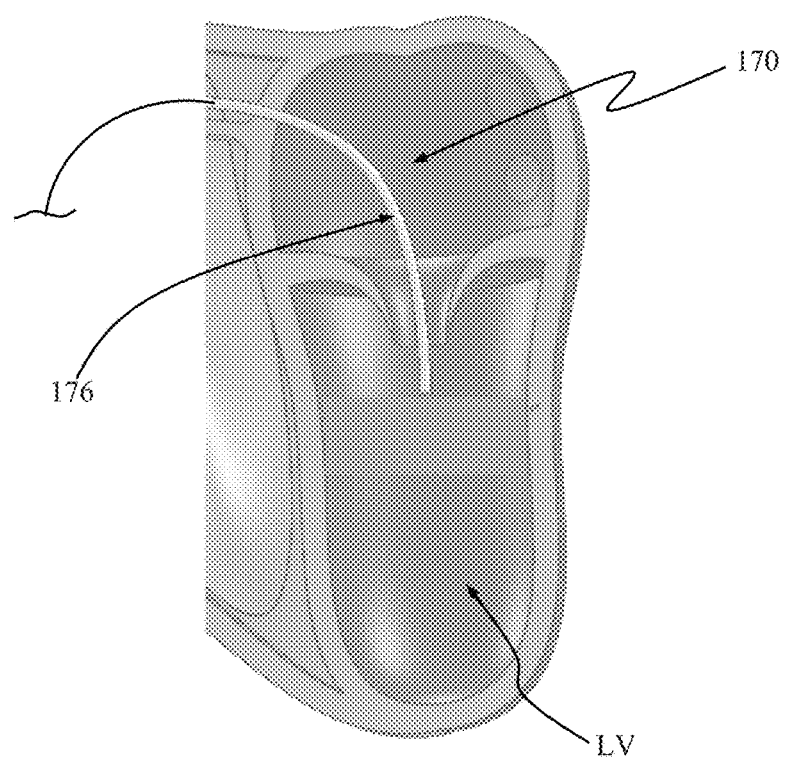
Figure 15B:
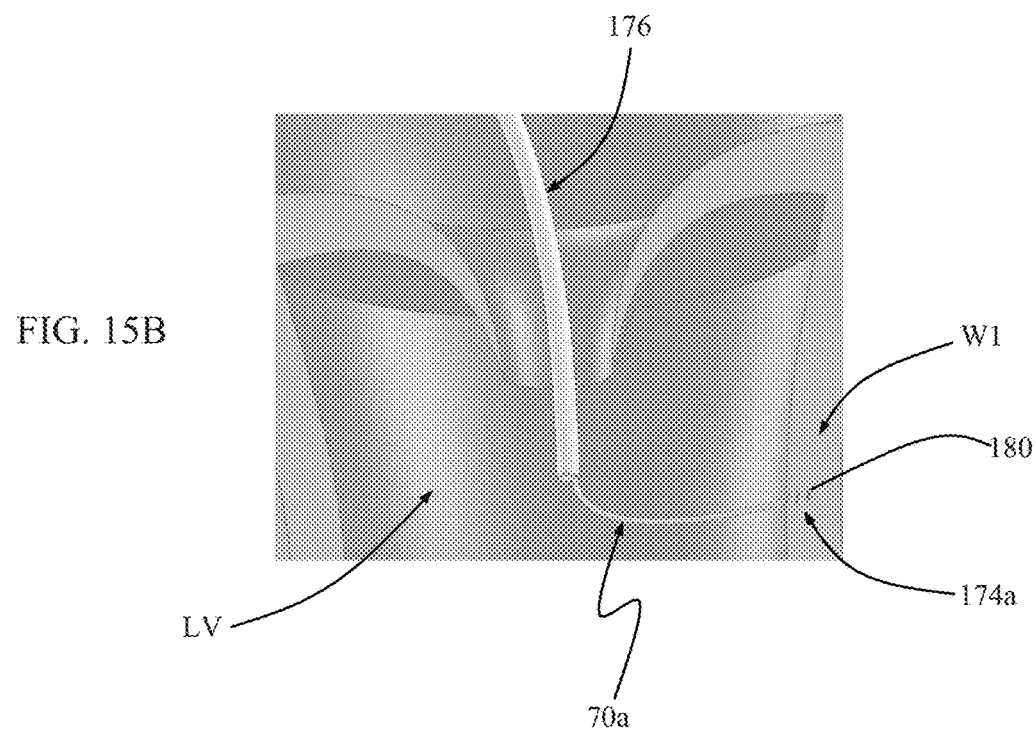

Some methods of the present disclosure making use of the guide member assembly 170 can a delivery arrangement wherein the docking structures 174a, 174b, 174c are positioned within the outer sheath 176. The so-loaded outer sheath 176 is then steered or advanced over a guidewire and into the left ventricle LV as in FIG. 15A. The outer sheath 176 is then manipulated (e.g., retracted, steered, etc.) to expose the anchor body 180 of the first docking structure 174a. The corresponding elongated member 70a is then manipulated to directing the docking structure 174a toward a native tissue wall section W1 of the left ventricle LV as in FIG. 15B. The anchor body 180 can be a sharpened coil or screw that readily digs into the anatomy as shown in FIG. 15C. The first elongated member 70a is rotated, applying a torque onto the first docking structure 174a to achieve robust engagement with the wall section W1. A tugging force can then be applied onto the first elongated member 70a to confirm that the anchor body 180 of the first docking structure 174a is embedded into the wall section W1. This same process is repeated for placing the second docking structure 174b into a separate wall section W2 (FIG. 15D), followed by placement of the third docking structure 174c into a separate wall section W3 (FIG. 15E). The delivery device (not shown) can then be advanced over the outer sheath 176 commensurate with the descriptions above. The guide member assembly 170 is configured such that by individually placing the three docking structures 174a, 174b, 174c independent of one another, the three elongated members 70a, 70b, 70c can be individually manipulated to effectively create steering at the tip of the outer sheath 176. Following deployment of the prosthetic heart valve (not shown) or other procedure, the elongated members 70a, 70b, 70c can be rotated or twisted to "unscrew" the corresponding docking structure 174a, 174b, 174c from the tissue wall. Once released, the guide member assembly 170 can be withdrawn from the patient.

Figure 16:
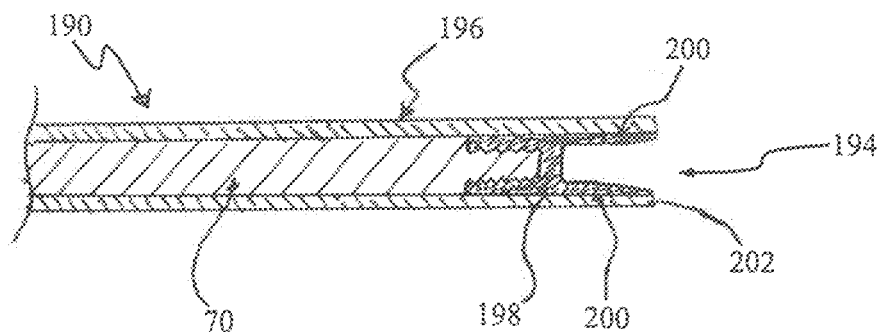
FIG. 16 is a simplified side view of another guide member assembly in accordance with principles of the present disclosure and useful with the systems and methods of the present disclosure.

Another embodiment guide member assembly 190 in accordance with principles of the present disclosure is shown in FIG. 16, and includes the elongated member 70 as described above along with a docking structure 194 and an outer sheath or jacket 196. The docking structure 194 can include a base 198 and two (or more) anchor members (e.g., barbs) 200. The base 198 is configured for selective attachment to a distal end of the elongated member 70. For example, the base 198 and the elongated member 70 can have complementary threaded surfaces; other temporary attachment constructions are also acceptable. The anchor members 200 project from the base 198 and can each terminate at a sharp tip appropriate for piercing tissue. The outer sheath 196 can be a thin wall sheath and is slidably disposed over the elongated member 70. In the delivery arrangement of FIG. 16, the outer sheath 196 is located over the docking structure 194, collapsing the anchor members 200 toward one another. The docking structure 194 is configured to self-transition to a capture or deployed arrangement when released from the outer sheath 196 as described below (e.g., as a distal end 202 of the outer sheath 196 is proximally retracted relative to the anchor members 200). For example, one or more portions of the docking structure 194 can be formed from a surgically safe metal or metal alloy (e.g., stainless steel, nitinol, etc.) shape set to self-revert to the capture or deployed arrangement.

Figure 17A:
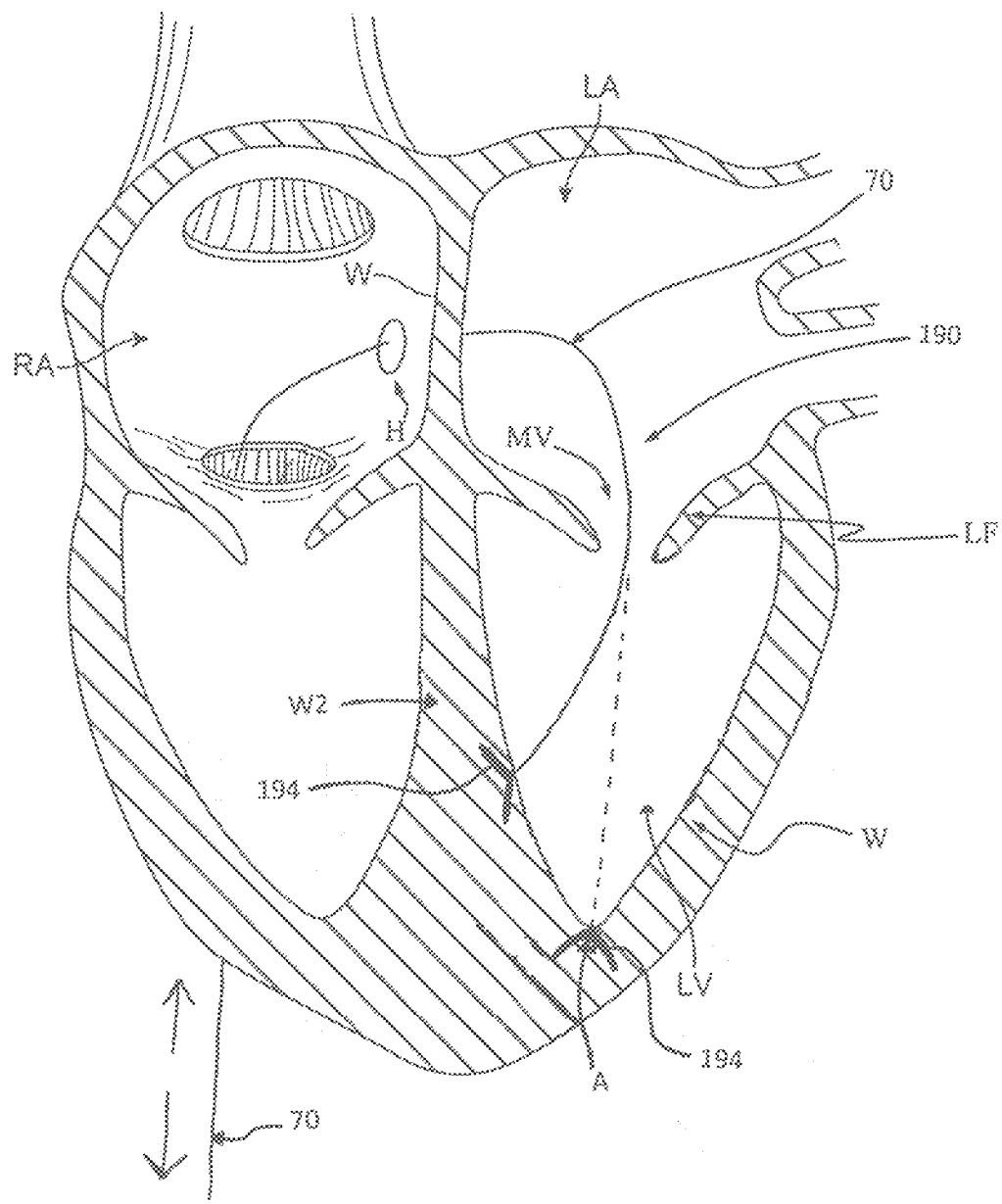
FIGS. 17A-17B illustrates methods of the present disclosure, including use of the guide member assembly of FIG. 16.
Figure 17B:
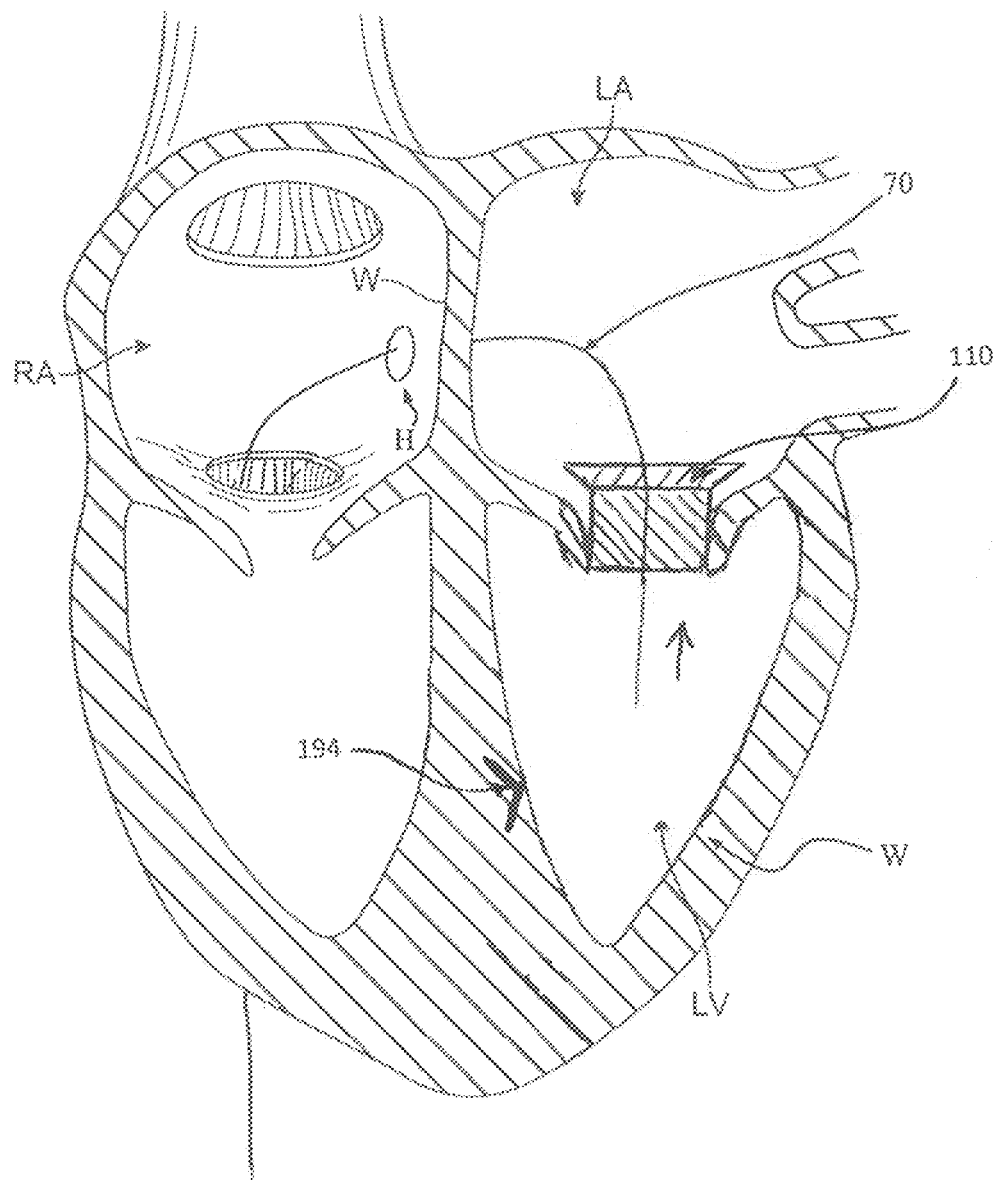

Some methods of the present disclosure making use of the guide member assembly 190 can include directing the guide member assembly 190, in the delivery arrangement, to the left ventricle LV (FIG. 5A) commensurate with the above explanations. The distal end 202 of the outer sheath 196 is located against the native anatomy structure of interest (e.g., a wall of the left ventricle LV). The outer sheath 196 is then retracted relative to the docking structure 194 (and/or the elongated member 70, and thus the docking structure 194, is distally advanced relative to the outer sheath 196); the anchor members 200 self-transition toward the capture or deployed arrangement, embedding into tissue of the heart wall. For example, FIG. 17A illustrates the docking structure 194 in the capture or deployed arrangement and engaged with the wall W2 of the left ventricle LV. Alternatively, and as shown with dashed lines, the docking structure 194 can be docked to an apex A of the left ventricle LV. Regardless, methods of the present disclosure can include tracking a delivery device (such as the delivery device 40 (FIG. 5A)) over the elongated member 70 of the now-docked or anchored guide member assembly 190, followed by deployment of the prosthetic heart valve 110 as shown in FIG. 17B. The elongated member 70 can then be disconnected from the docking structure 194 (e.g., the elongated member 70 can be rotated to unscrew or unthread from the docking structure 194). Once disconnected, the elongated member 70 can be removed from the patient, while the docking structure 194 remains in situ.

Figure 18:
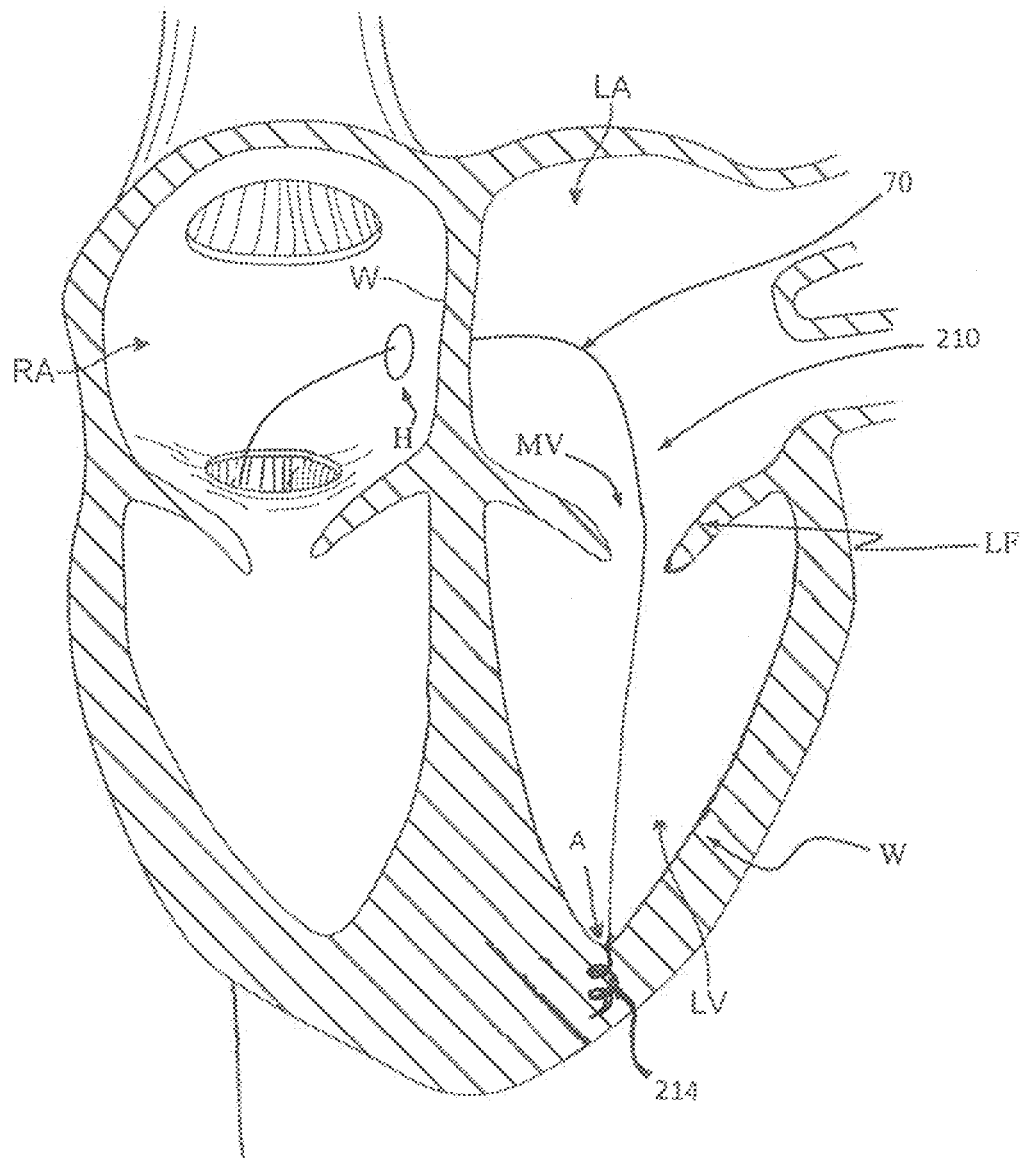
FIG. 18 is a simplified side view of another guide member assembly in accordance with principles of the present disclosure and in performing methods of the present disclosure.

Any of the docking structures of the present disclosure can be utilized with methods of the present disclosure in which the docking structure is docked to the apex A of the left ventricle LV. For example, another embodiment guide member assembly 210 is shown in FIG. 18, and includes the elongated member 70 and a docking structure 214 which may comprise a helix formed into or at the tip of the elongated member 70 (e.g. 0.032 inch diameter elongated member). The guide member assembly 210 has been delivered (e.g., via a small diameter delivery system) through the inter-arterial septum, and then through the mitral valve MV. The docking structure 214 has then been anchored to native anatomy of the walls W of the left ventricle LV at or near the apex A. The so-docked guide member assembly 210 provides a stable rail that a large diameter delivery system (e.g., the delivery device 40 (FIG. 5B)) can be advanced, tracked, or guided over as described above.

Figure 19:
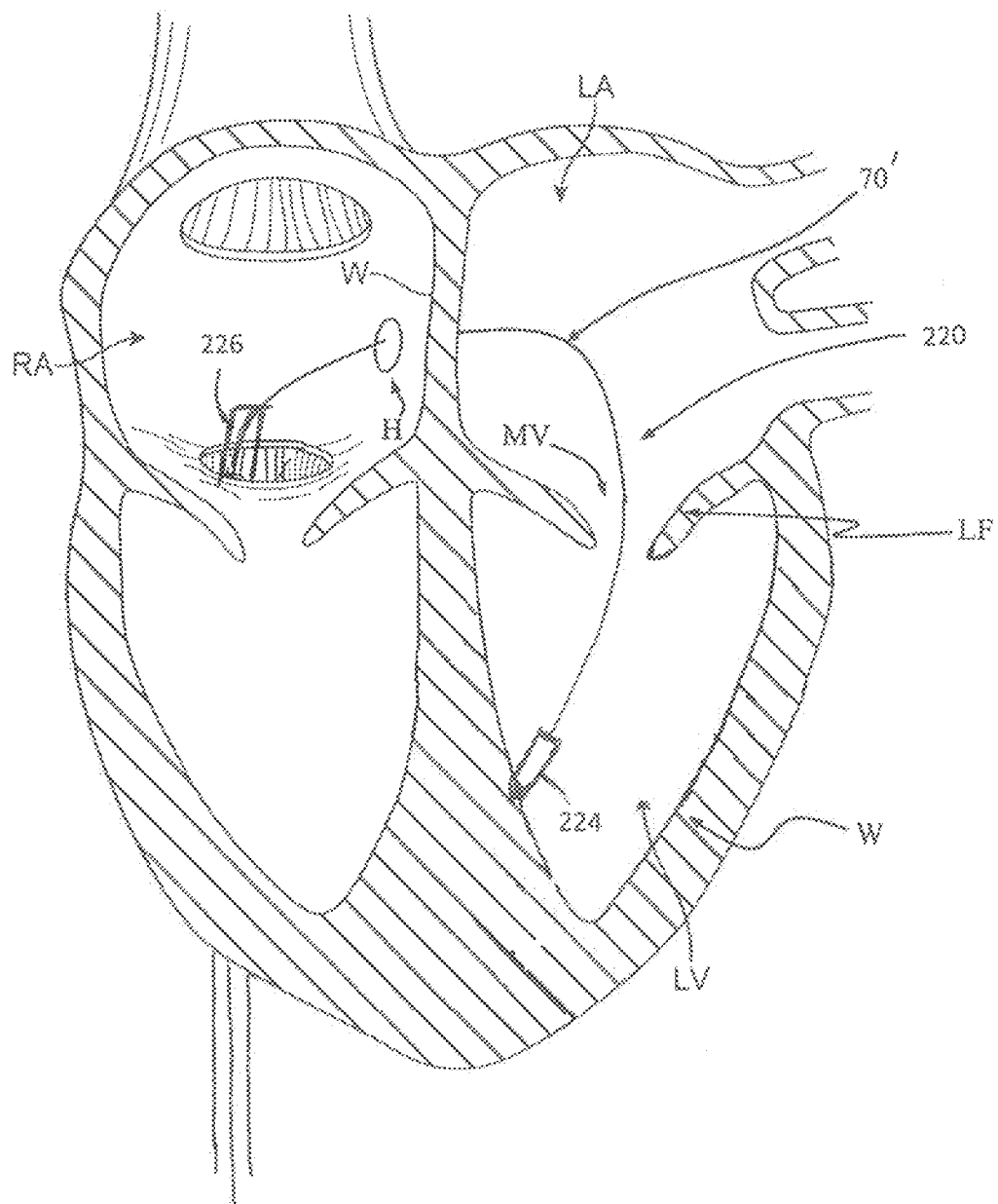
FIG. 19 is a simplified side view of another guide member assembly in accordance with principles of the present disclosure and in performing methods of the present disclosure.

As mentioned above, with any of the guide member assemblies of the present disclosure, the elongated member 70 can be configured to self-assume or be biased toward (e.g., formed of a shape memory material) a predetermined shape or curvature that is beneficial for particular procedures. For example, another embodiment guide member assembly 220 in accordance with principles of the present disclosure is shown in FIG. 19. The guide member assembly 220 includes an elongated member 70' connected to a docking structure 224, and a delivery tube 226. The docking structure 224 can assume any of the formats or constructions described through the present disclosure, and is generally configured to engage or anchor to native tissue. The elongated member 70' can be akin to conventional guidewire constructions known in the art, but is formed to self-assume the curved shape as shown. The curvature and other dimensions or geometries of the pre-determined shape correspond with transseptal advancement of the elongated member 70' to the left ventricle LV and docking of the docking structure 224 to native anatomy. The predetermined shape naturally locates the elongated member 70' through the mitral valve MV and within the septum; with this arrangement, as the elongated member 70' is delivered and a delivery device (not shown) tracked over the elongated member 70', the elongated member 70' will not exert significant forces on tissue of the septum (a problem known as "cheese grating" with conventional flossing techniques). The delivery tube 226 can be relatively more rigid than the elongated member 70', and assists in temporarily straightening the pre-formed curvature in the elongated member 70' for initial delivery to the heart.

Returning to FIG. 4, in some optional embodiments, both the elongated member 70 and the docking structure 72 include electrically conductive materials (e.g., the elongated member 70 can include an electrically conductive metal wire surrounded by an electrical insulator, and the docking structure includes a metal hook, coil, barb, clip, tine, etc., that is electrically connected to the metal wire). With these and similar constructions, the guide member assembly 60 can further include (or be connected to) a source of energy (e.g., a pacing device), and can be configured to perform various electrical energy-type procedures on a patient as part of, for example, transseptal delivery of a prosthetic mitral valve. With these and related embodiments, the guide member assembly 60 can serve as a pacing lead, for example, in addition to providing the delivery device tracking features described above. With these and related embodiments, once the docking structure 72 is in contact with native tissue of interest, the guide member assembly 60 can be operated as a temporary cardiac pacing wire, and allows for rapid pacing of the patient's heart during deployment of the prosthetic heart valve. The pacing or other electrical energy related procedures could be performed on the left ventricle LV (FIG. 1) or other areas of the patient's heart (e.g., the left atrium LA (FIG. 1)). As a point of reference, conventional pacing leads are too flexible or do not otherwise have sufficient rigidity for tracking of a transcatheter prosthetic heart valve delivery device loaded with a compressed prosthetic heart valve. In contrast, the guide member assemblies of the present disclosure (such as with some embodiments of the elongated member 70) are mechanically robust, capable of traversing a tortuous pathway and capable of directing a tracked transcatheter prosthetic heart valve delivery device along a curved pathway.

Figure 8:
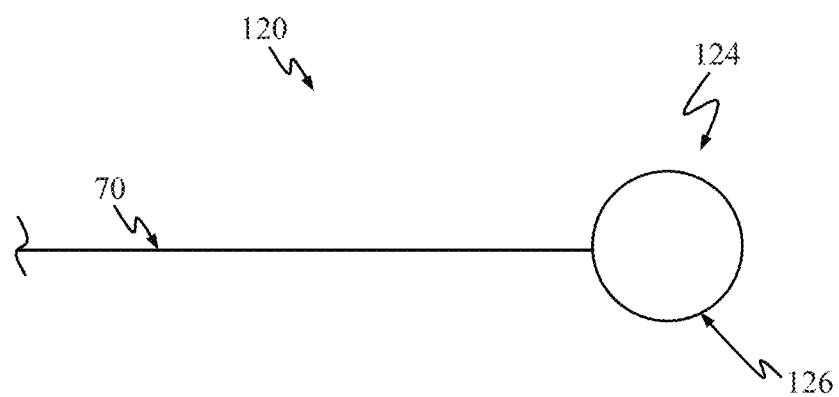
FIG. 8 is a simplified side view of another guide member assembly in accordance with principles of the present disclosure and useful with the systems and methods of the present disclosure.
Figure 9:
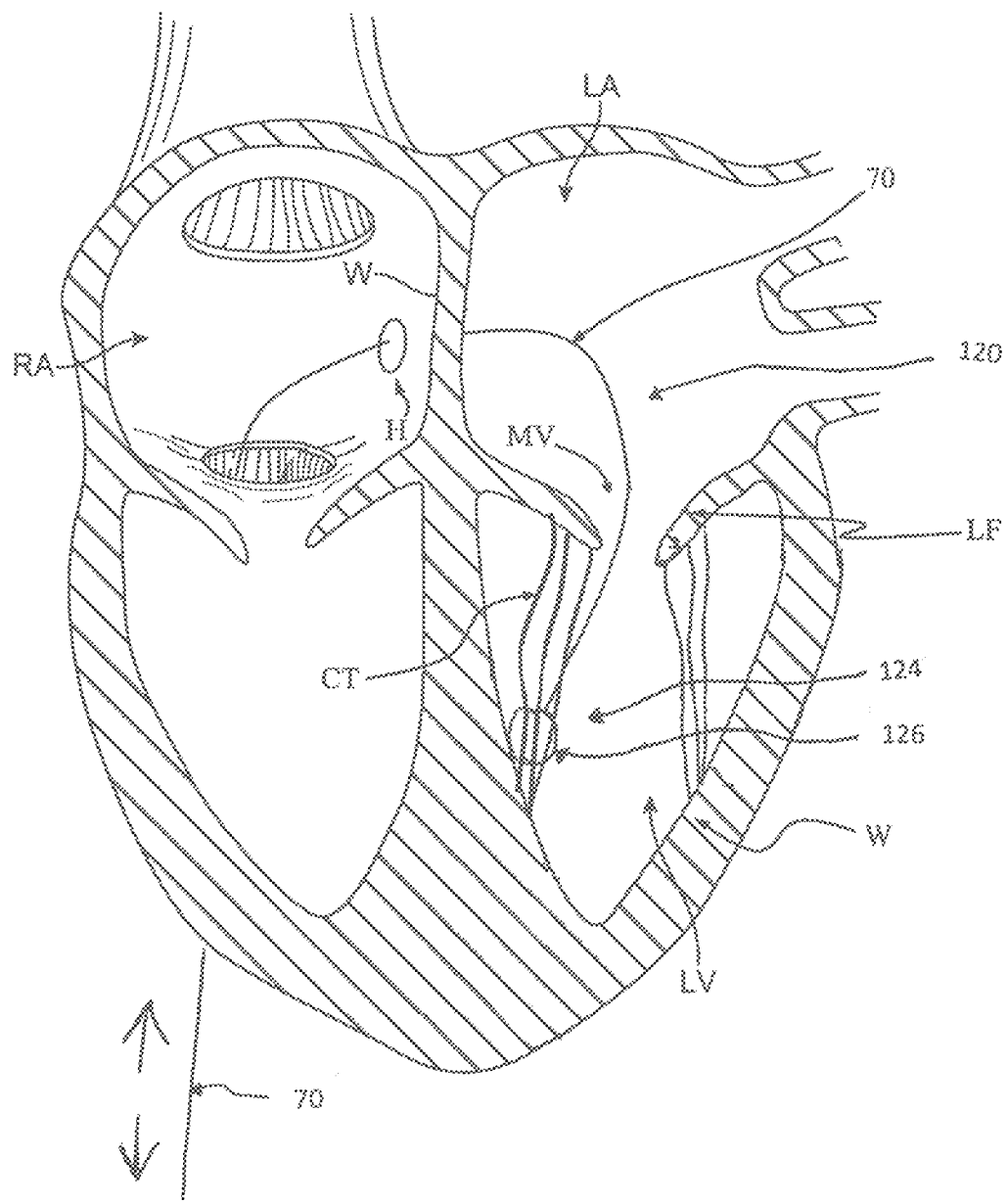
FIG. 9 illustrates methods of the present disclosure, including use of the guide member assembly of FIG. 8.
Figure 20:
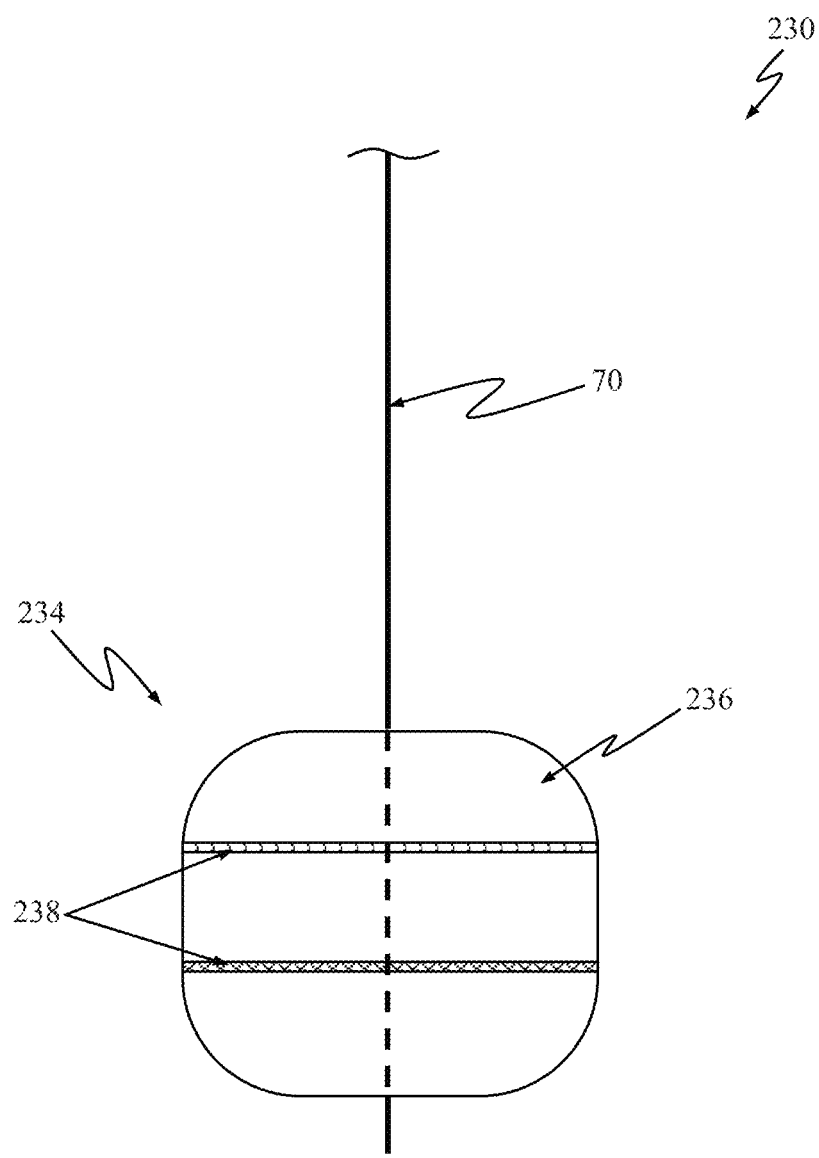
FIG. 20 is a simplified side view of another guide member assembly in accordance with principles of the present disclosure and useful with the systems and methods of the present disclosure.

As mentioned above, in some embodiments, the docking structure 72 can be or include an inflatable anchor member (e.g., the docking structure 124 of FIG. 8). With these and related embodiments, the inflatable docking structure can be configured (e.g., inflated size and shape) to engage or anchor against various native structures of the patient's heart. For example, another embodiment guide member assembly 230 in accordance with principles of the present disclosure is shown in FIG. 20. The guide member assembly 230 includes the elongated member 70 as described above, along with a docking structure 234. The docking structure 234 includes an inflatable anchor member 236 (e.g., a balloon) and optional grip bodies 238. The inflatable anchor member 236 can be directly attached to the elongated member 70 (with the elongated member 70 having a lumen for delivering an inflation medium to an interior of the inflatable member 236). Alternatively, the inflatable anchor member 236 can be provided as part of a balloon catheter that is slidably disposed over the elongated member 70 and forms requisite inflation lumen(s). Regardless, the inflatable anchor member 236 is transitionable between a delivery arrangement (not shown) and the capture or deployed arrangement of FIG. 20 (in which the inflatable anchor member 236 has been inflated); in the capture or deployed arrangement, the inflatable anchor member 236 is sized and shaped to lodge or anchor in the left ventricle LV (FIG. 1) as described in greater detail below.

Figure 21:
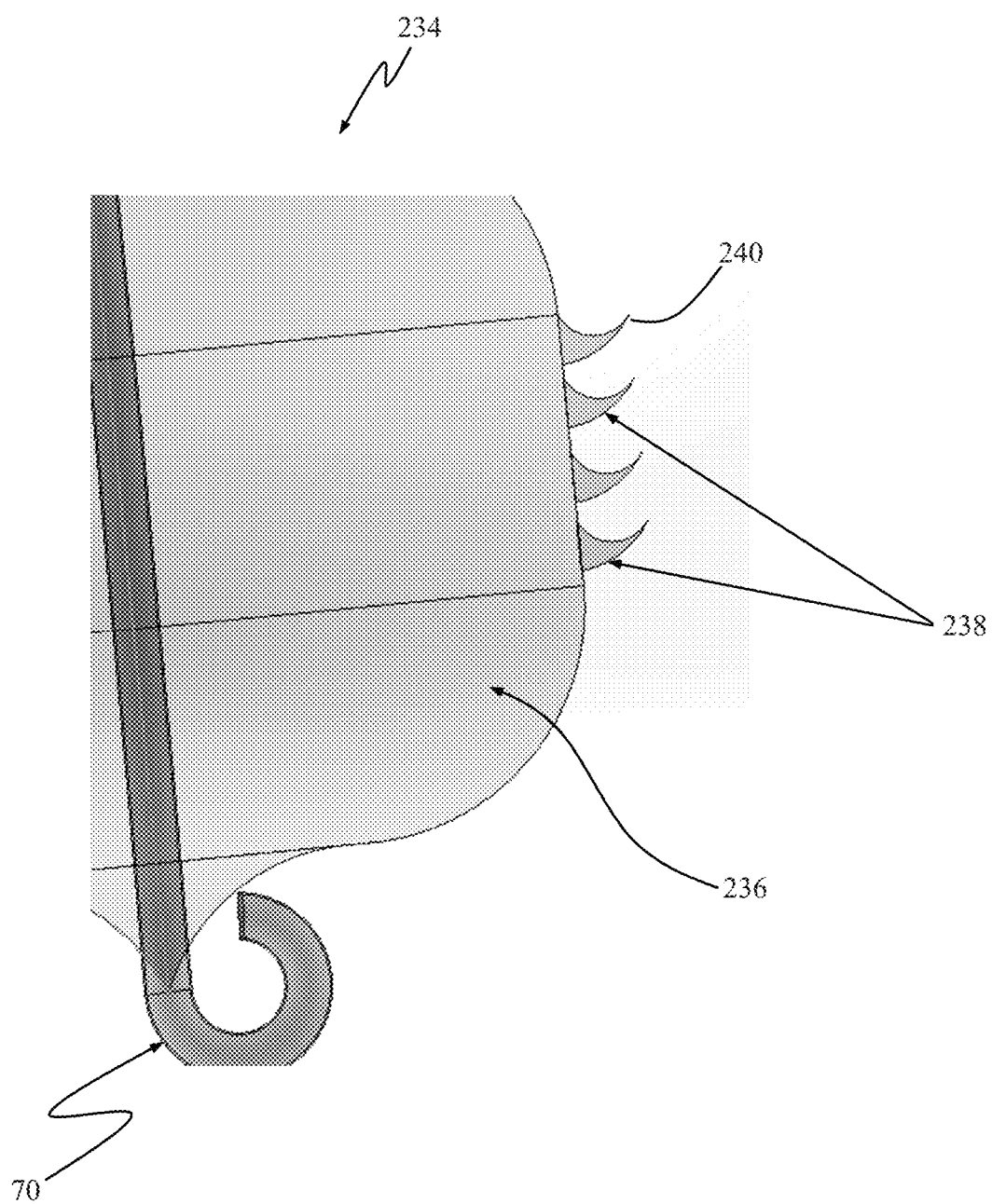
FIG. 21 is an enlarged side view of a portion of a docking structure of the guide member assembly of FIG. 20.

The grip bodies 238, where provided, are carried on an exterior of the inflatable anchor member 236 and are configured to provide a more robust engagement or purchase with native tissue. The grip bodies 238 can assume various forms, and in some embodiment have a directional bias for reasons made clear below. In some non-limiting embodiments reflected by FIG. 21, the grip bodies 238 can be akin to scales or ribs, projecting from the inflatable anchor member 236 to a tip (e.g. sharp tip) 240. A shape or profile of one or more of the grip bodies 238 can be such that tip 240 is biased away from a distal end 242 of the inflatable member 236. With this construction, the grip bodies 238 will more overtly resist a pulling force in the proximal direction, and will more easily "slip" in response to a force in the distal direction. This "biased" attribute can be provided with a number of other configurations. For example, the grip bodies 238 can be a number of extremely stiff and flat arms that naturally project perpendicular to the surface of the inflatable anchor member 236 when the inflatable anchor member 236 is inflated/expanded; when the inflatable anchor member 236 is deflated, the stiff and flat arms can readily "flip" in any direction. With this optional construction, the grip bodies 238 promote robust engagement of the docking structure 234 with native anatomy with expansion of the inflatable anchor member 236, and allow the docking structure 234 to easily release from the native anatomy with deflation of the inflatable anchor member 236. The grip bodies 238 can be relatively large and sturdy as shown. In other embodiment, the grip bodies 238 can have a very small scale (e.g., micro-sized bodies) and are disposed over a larger surface area of the inflatable anchor member 236.

Figure 22B:
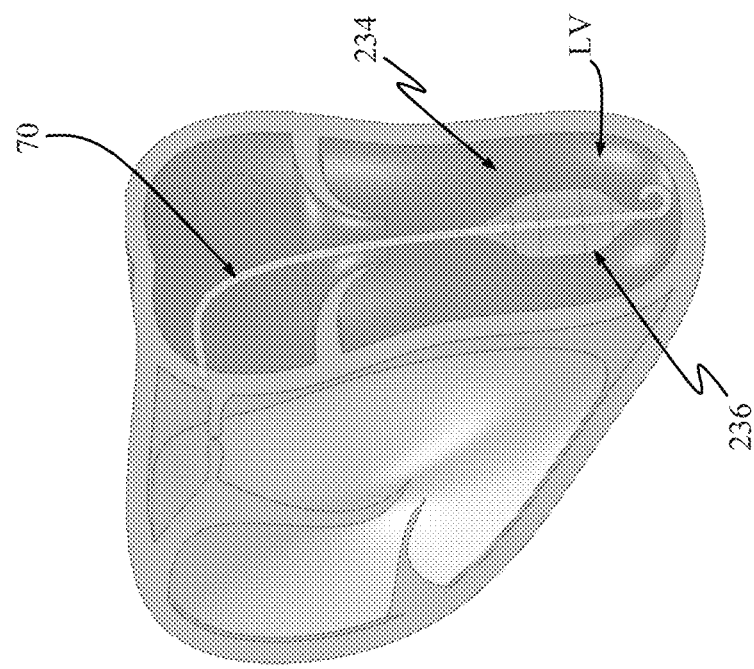
FIGS. 22A-22D illustrates methods of the present disclosure, including use of the guide member assembly of FIG. 20.
Figure 22A:
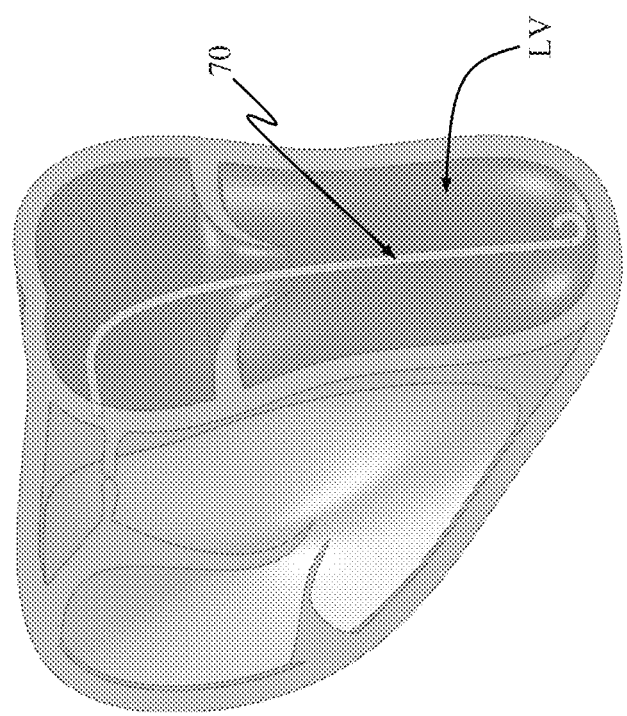
Figure 22C:
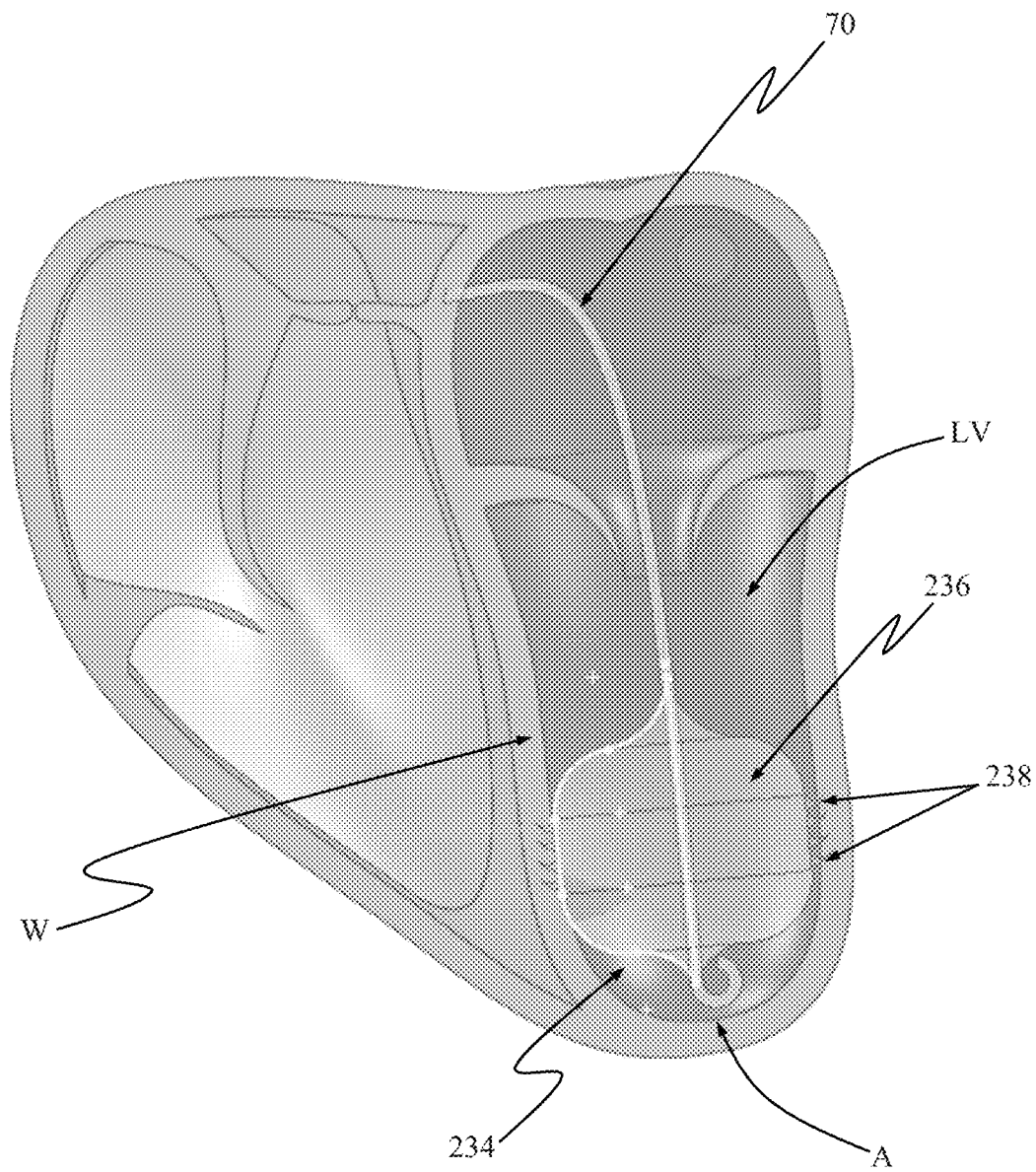
Figure 22D:
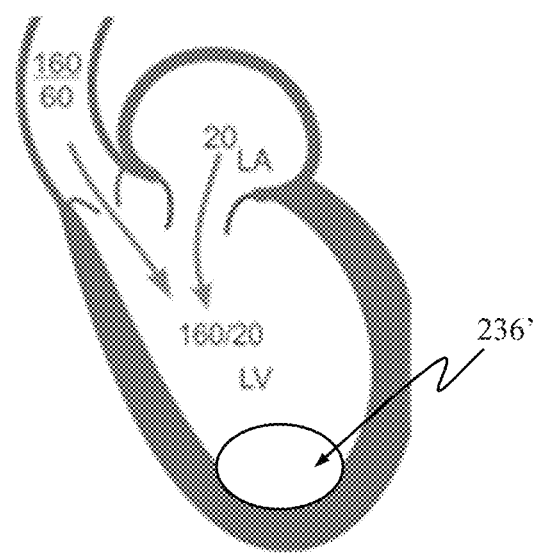

Some methods of the present disclosure making use of the guide member assembly 230 can include transseptally inserting a elongated member, such as the elongated member 70, into the left ventricle LV as in FIG. 22A. The docking structure 234 (with the inflatable anchor member 236 deflated) is then advanced to the bottom of the left ventricle LV as in FIG. 22B. The docking structure 234 can be carried by the elongated member 70, can be slidably disposed over the elongated member 70, the previously-inserted elongated member can be replaced by the elongated member 70 otherwise carrying the docking structure 234. Regardless, and with additional reference to FIG. 22C, the inflatable anchor member 236 is pressed deep into the left ventricle LV (e.g., at the apex A) and constant pressure is held while the inflatable anchor member 236 is inflated. As the inflatable anchor member 236 inflates, it presses against the apex A and begins to push upwards. As the inflatable anchor member 236 comes into contact with the complex wall structure W of the left ventricle LV, the grip bodies 238 intimately catch into the wall structure W. The docking structure 234 thus becomes lodged in the left ventricle LV, effectively anchoring the elongated member 70. The so-docked guide member assembly 230 provides a stable rail that a larger diameter delivery system (e.g., the delivery device 40 (FIG. 5B)) can be tracked over as described above. Because the inflatable anchor member 236 is in place on the elongated member 70, in some embodiments the tip of the delivery device is a rapid exchange (Rx) style tip in order to allow for the larger diameter of the docking structure 234 without forcing the delivery system to have an increased diameter. As a point of reference, the expanded inflatable anchor member 236 is shown in FIG. 22C as occupying a fairly large volume of the left ventricle LV for ease of understanding. In other embodiments, the inflatable anchor member 236 is sized and shaped to occupy less than a majority (e.g., no more than 25%, alternatively approximately 20%) of an available volume of the left ventricle LV as generally reflected by the inflatable anchor member 236' shown in FIG. 22D. It will be understood that the expanded inflatable anchor member 236' will reduce the open volume of the left ventricle LV and may impede some level of contraction above the inflatable anchor member 236', but not prevent it. In some embodiments, the inflatable anchor member 236' is made as small as possible while still achieving a desired level of grip to the native anatomy.

Figure 23:
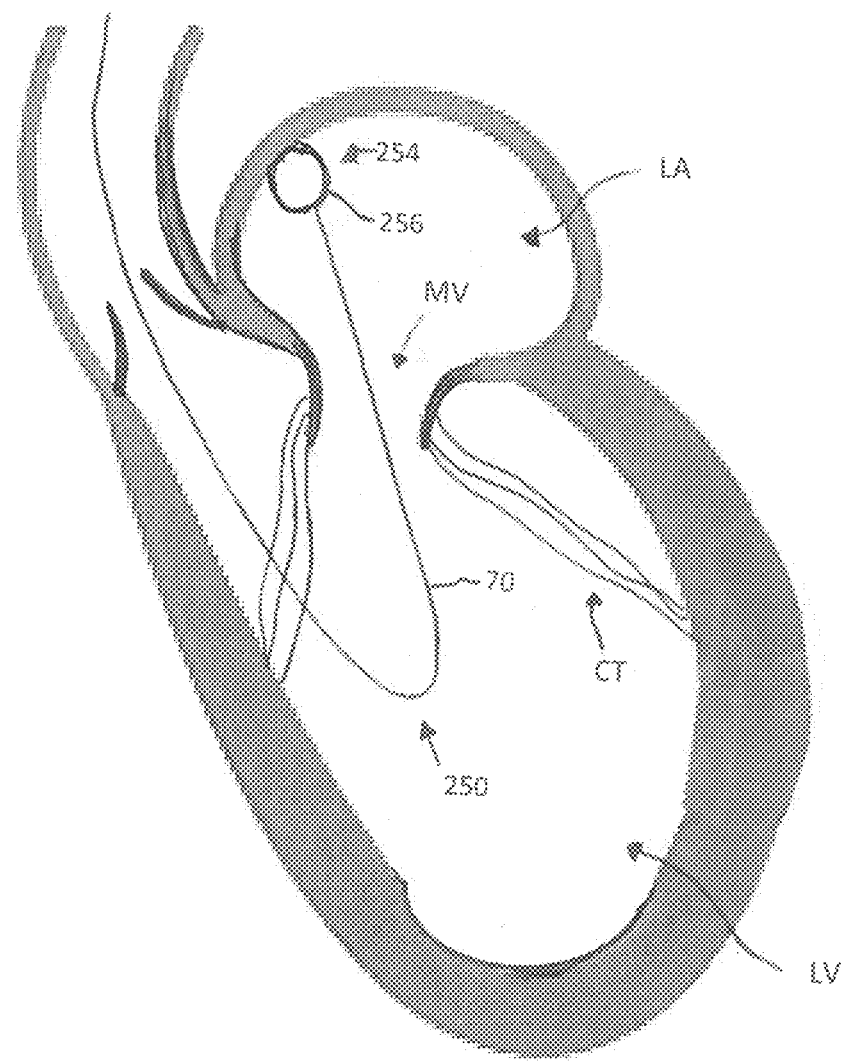
FIG. 23 is a simplified side view of another guide member assembly in accordance with principles of the present disclosure and in performing methods of the present disclosure.

While some methods described above entail use of a guide member assembly of the present disclosure in performing a transseptal access to the mitral valve and anchoring or docking at or within the left ventricle to facilitate delivery of a prosthetic mitral valve, other surgical approaches are also envisioned by the present disclosure. For example, FIG. 23 illustrates another embodiment guide member assembly 250 in performing a retrograde aortic access or delivery procedure. The guide member assembly 250 includes the elongated member 70 as described above, along with a docking structure 254. The docking structure 254 can assume any of the formats described in the present disclosure, and in some embodiments is or includes an inflatable anchor member (e.g., a balloon) 256. To attain the arrangement of FIG. 23, the elongated member 70 is advanced to the left ventricle LV via a retrograde aortic approach and then toward the mitral valve MV. In this regard, the inflatable anchor member 256 can assist in navigating through the chordae CT in the left ventricle LV, for example by slightly inflating the inflatable anchor member 256, may better ensure that the elongated member 70 has a clear path to the center of the mitral valve MV. Once located in the left atrium LA, the docking structure 254 can be operated or manipulated to dock to native anatomy as described above. Once anchored, the elongated member 70 is stabilized for tracking of a prosthetic heart valve delivery device commensurate with the descriptions above.

Figure 24:
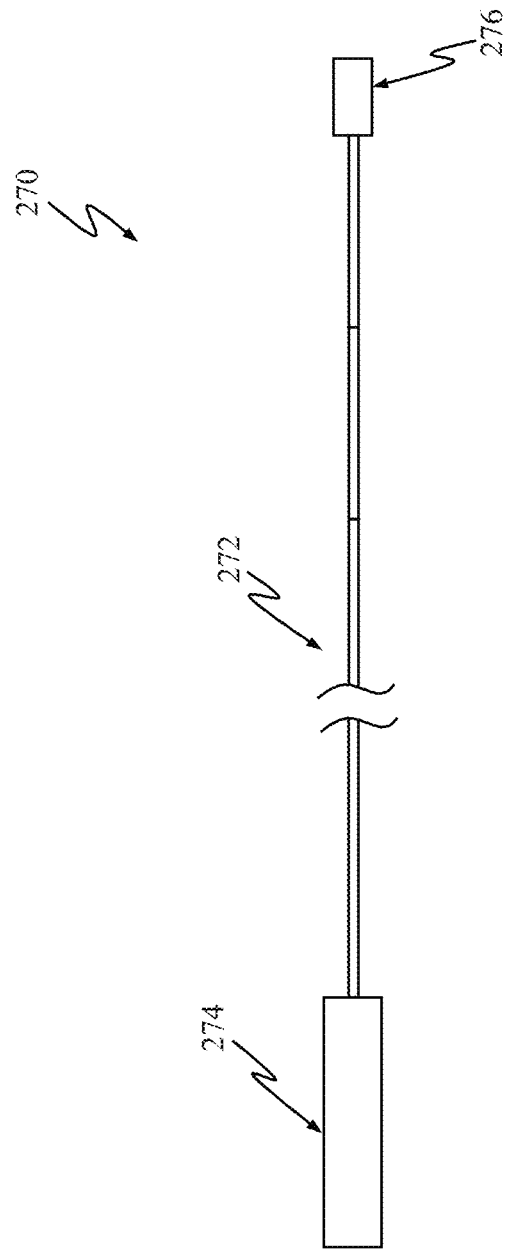
FIG. 24 is a simplified side view of another guide member assembly in accordance with principles of the present disclosure and useful with the systems and methods of the present disclosure.
Figure 25:
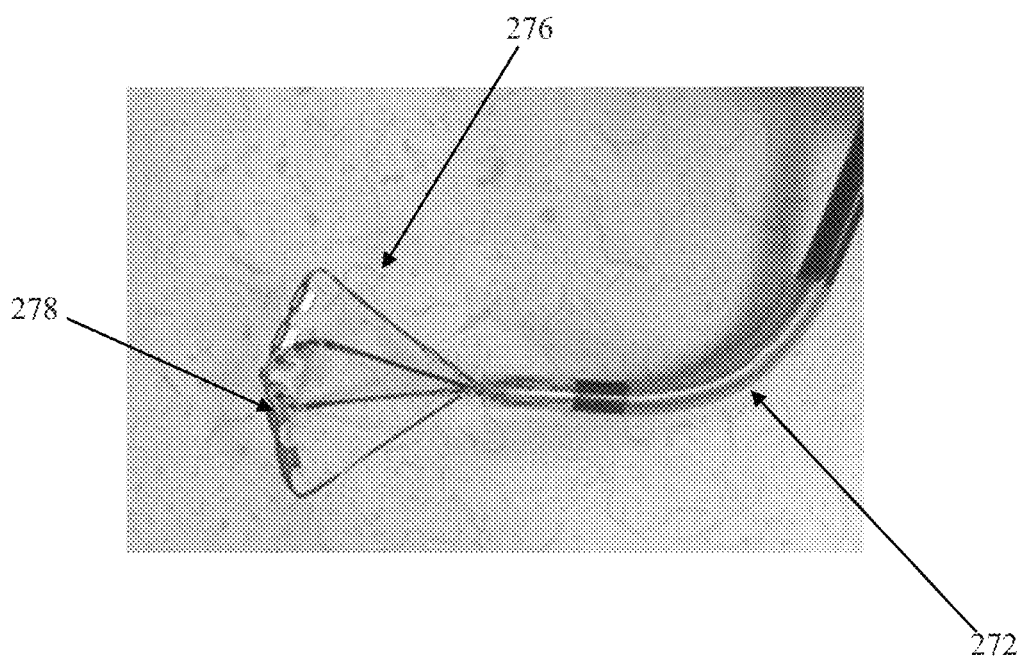
FIG. 25 is a photograph of a portion of the guide member assembly of FIG. 24.

In some embodiments of the present disclosure, any of the guide member assemblies disclosed herein can incorporate a steerable elongated member or rail. For example, another guide member assembly 270 in accordance with principles of the present disclosure is shown in FIG. 24 and includes a steerable rail or elongated member 272, a handle 274, and an optional docking structure 276. The steerable elongated member 272 can assume various forms known in the art appropriate for providing steering capabilities. For example, two or more rail or rod segments can by pivotably (and/or rotatably) coupled to one another, and pull wires (or other actuators) provided; an operator can manipulate or steer the rod segment relative to one another via the handle 274. Other steering features known in the catheter art, for example, can be incorporated into the steerable elongated member 272 (e.g., hydraulic-based steering mechanisms). Regardless, during a surgical procedure, such as the transseptal prosthetic mitral valve delivery procedures described above, the prosthetic mitral valve delivery device (e.g., the delivery device 40 of FIG. 4) rides or tracks over the steerable elongated member 272. As the capsule 52 (FIG. 4) and thus the collapsed prosthetic mitral valve constrained therein pass from the right atrium into the left atrium, and then into the left ventricle, the pull wires (or other actuators) can be operated or manipulated to alter or articulate the shape of the steerable elongated member 272. As the capsule/collapsed valve enters the native mitral valve annulus, additional steering of the distal end of the steerable elongated member 272 located deep in the left ventricle could help to center the prosthetic heart valve in the native valve annulus. With related methods, the steerable elongated member 272 can be used by pushing against the walls of the heart chamber(s) to deflect the prosthetic heart valve delivery device into a desired position.

Where provided, the optional docking structure 276 can assume various forms. In some embodiments, the docking structure 276 is configured to facilitate desired deflection of the steerable elongated member 272 against native anatomy. In some embodiments, the docking structure 276 can be or include a basket-type body 278 as shown in FIG. 25. The basket 278 may more effectively push the steerable elongated member 272 and therefor aid in orientating the prosthetic heart valve delivery device toward the center of the native mitral valve annulus.

Figure 26:
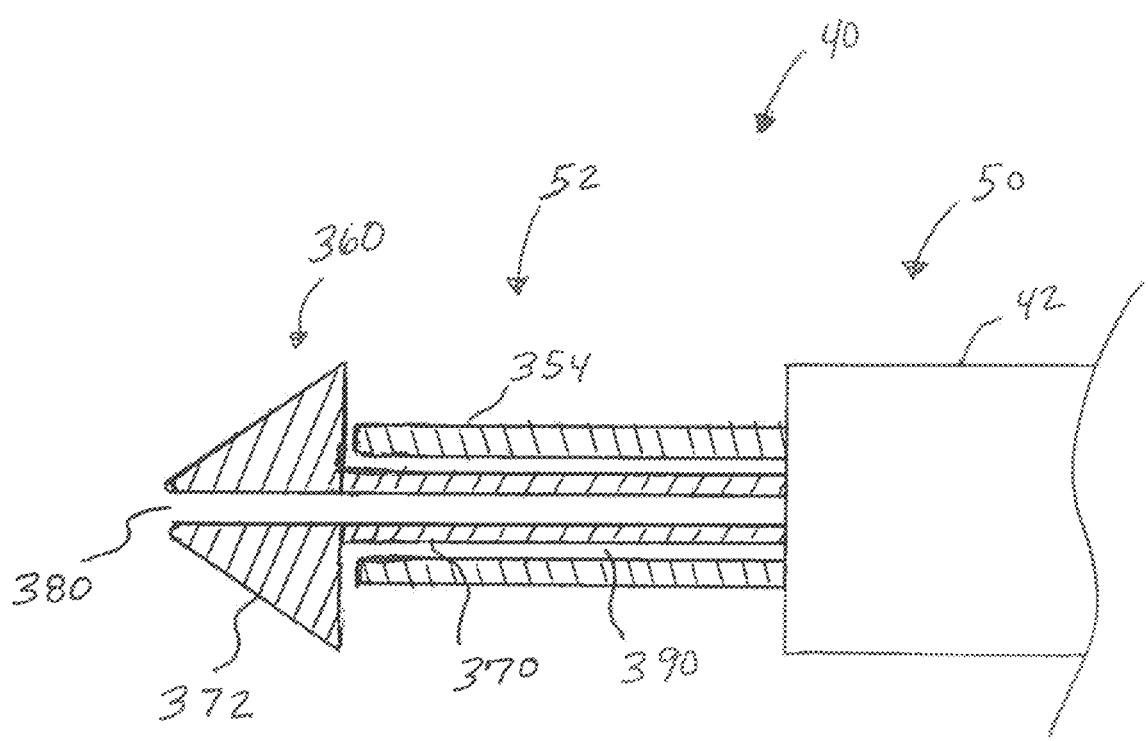
FIG. 26 is a simplified side view of a distal portion of a delivery device in accordance with principles of the present disclosure and useful with the systems and methods of the present disclosure.

As mentioned above, in some embodiments, any of the docking structures of the present disclosure can alternatively be provided as part of the delivery device 40, e.g., a guide member assembly 360 can be provided as part of the delivery device 40 wherein the guide member assembly 360 includes a docking structure 372, which can also be configured as a tip or nosecone for delivery device 40, and an elongated member 370 (FIG. 26). In some embodiments, the delivery device 40 can include a delivery sheath assembly 50, a support shaft assembly 52, a handle assembly 54 (FIG. 4), and a guide member assembly 360 wherein the delivery device 40 provides a loaded or delivery state in which a prosthetic valve is loaded over the support shaft assembly 52 and is retained within the capsule 42 of the delivery sheath assembly 50. The guide member assembly 360 includes a docking structure 372 carried by or connected to the distal end of the elongated member 370. The docking structure 372 is generally configured to interface or dock with expected anatomy. A guidewire lumen 380 can be provided through the docking structure 372 and through the elongated member 370 and can be open to a guidewire port (e.g., at the handle assembly 54). The support shaft assembly 52 can include an inner shaft 354 having a guide member lumen 390. The docking structure 372 can be advanced from the distal end of the inner shaft 354 via manipulation or advancement of the elongated member 370 through the lumen 390 of the inner shaft 354. The docking structure 372 is configured to engage native anatomy as described above. Once the docking structure 372 is relatively fixed to the native anatomy, a push/pull tension can be applied to the elongated member 370 allowing the support shaft assembly 52 and the delivery sheath assembly 50 of the delivery device 40 to be more readily distally advanced over the elongated member 370. Further, because the elongated member 370 can be generally aligned with the mitral valve MV via the docked docking structure 372, the capsule 42 will be similarly directed into and aligned with the mitral valve MV. The delivery device 40 is then operated to deploy the prosthetic heart valve.

In some embodiments, the docking structure 372 can be configured to transition (e.g., expand and collapse) between a delivery arrangement wherein the docking structure 372 is configured for use as a tip or nosecone for delivery device 40 and a deployed or capture arrangement wherein the docking structure 372 is used to engage native anatomy as described above. In some embodiments, the docking structure 372 can be selectively detachable from the elongated member 370 as described above. In some embodiments, the docking structure 372 can include one or more anchor members as described above.

Figure 27:
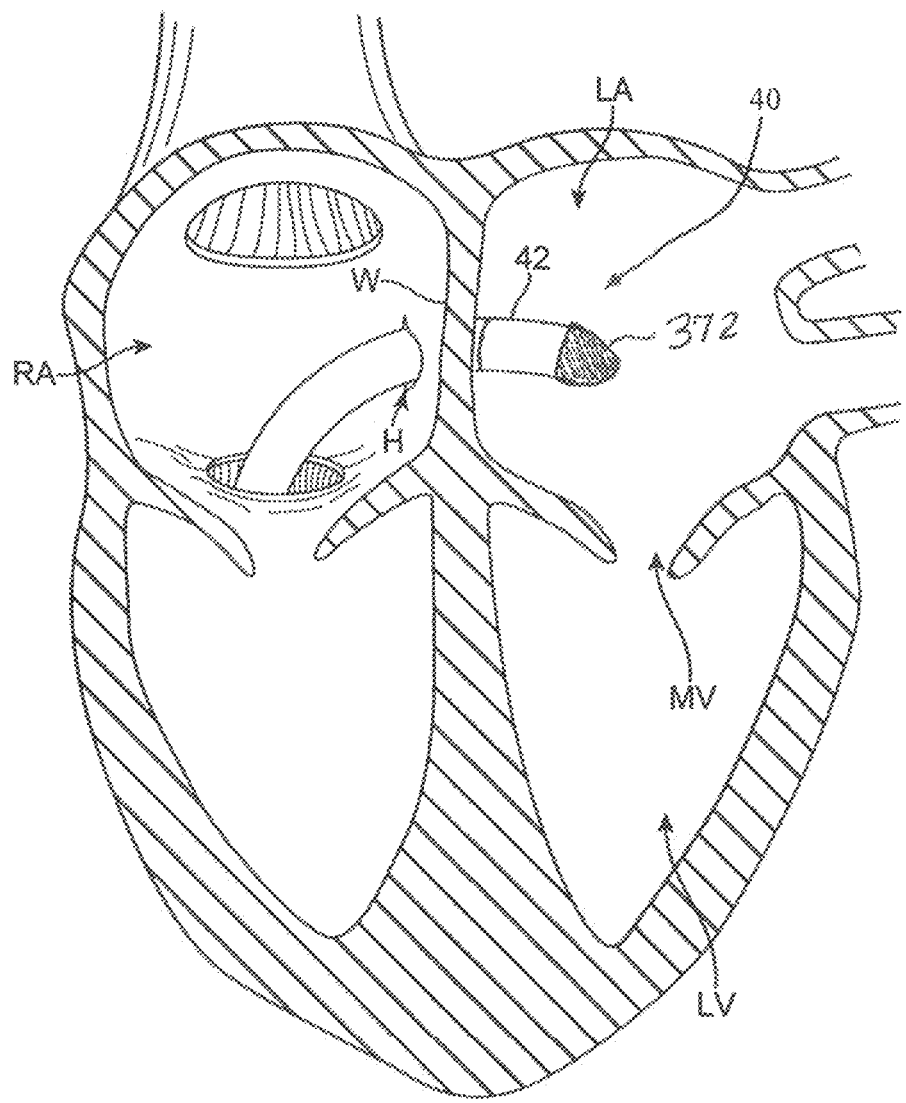
FIG. 27 is a simplified sectional view of a human heat and illustrating a distal end portion of a delivery device in accordance with principles of the present disclosure having attained transseptal access of the left atrium.
Figure 28:
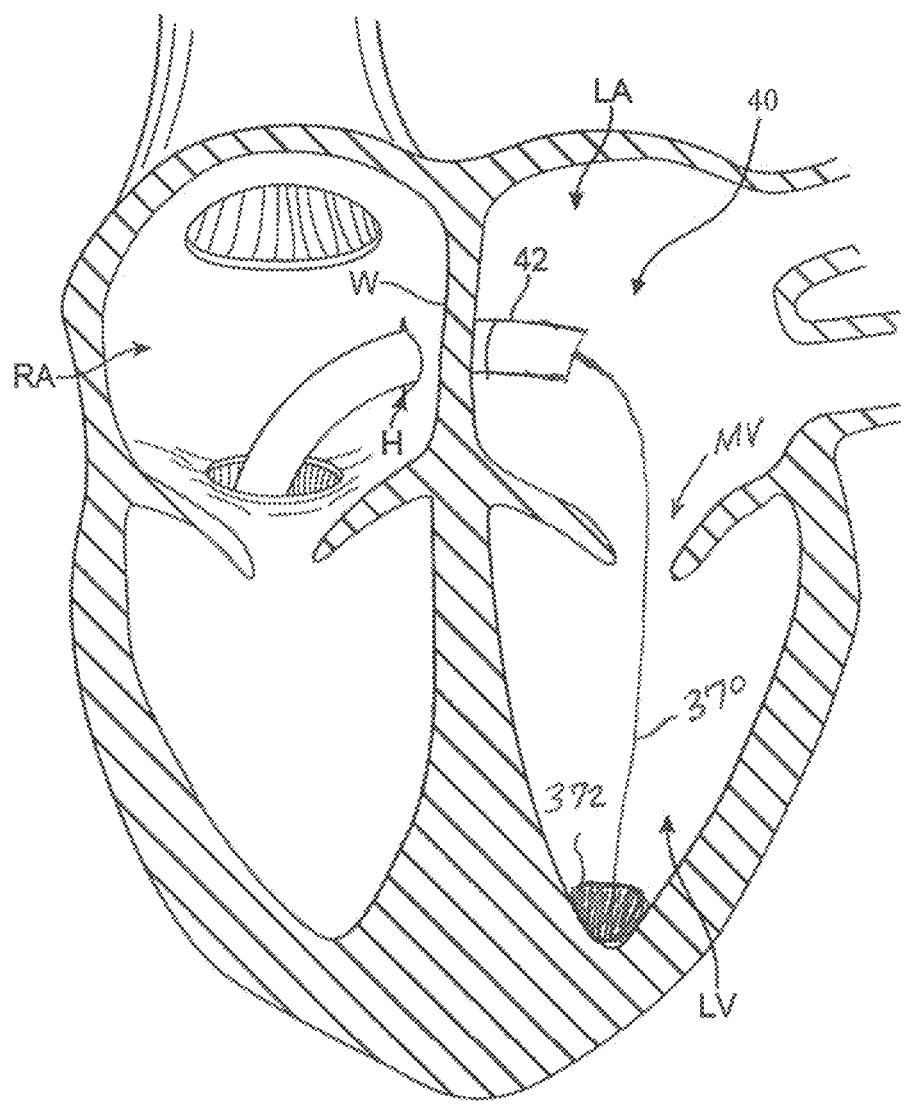
FIGS. 28-31 illustrate a method in accordance with principles of the present disclosure.
Figure 29:
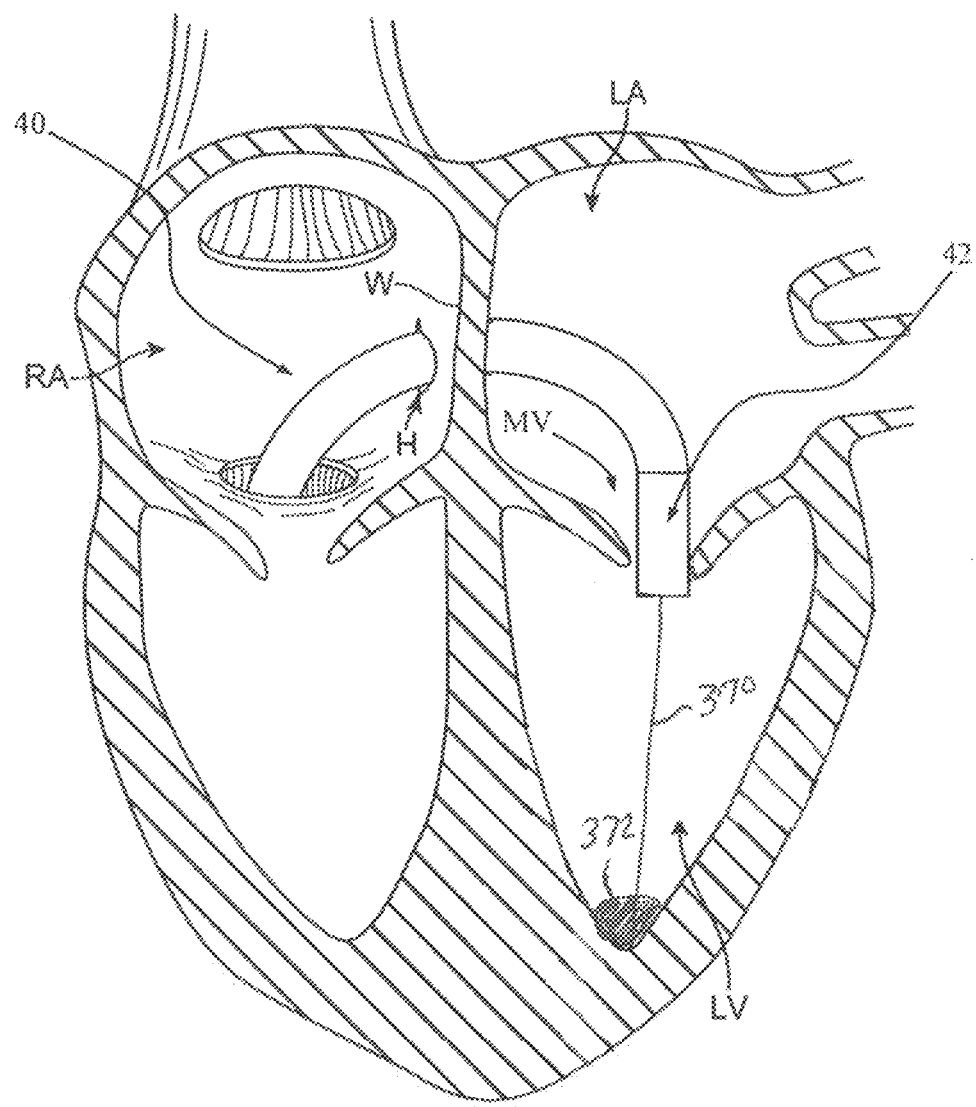
Figure 30:
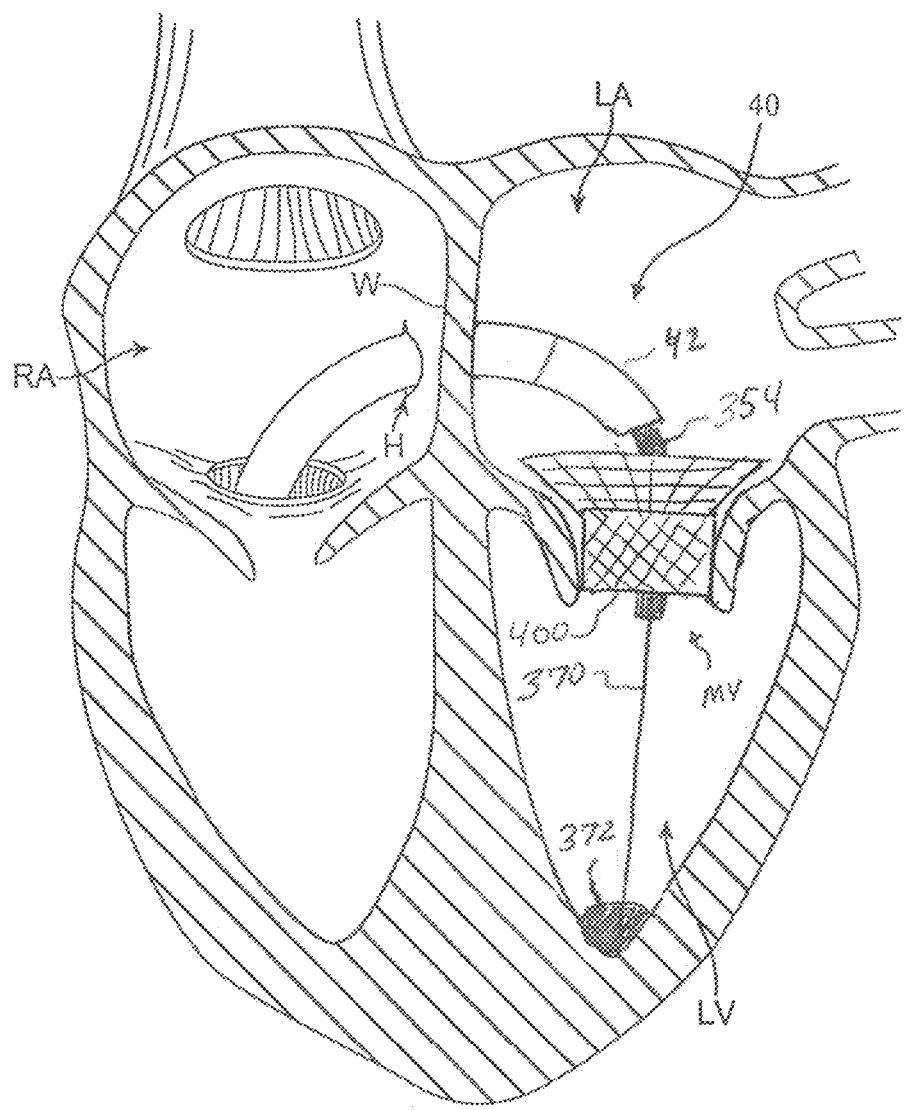
Figure 31:
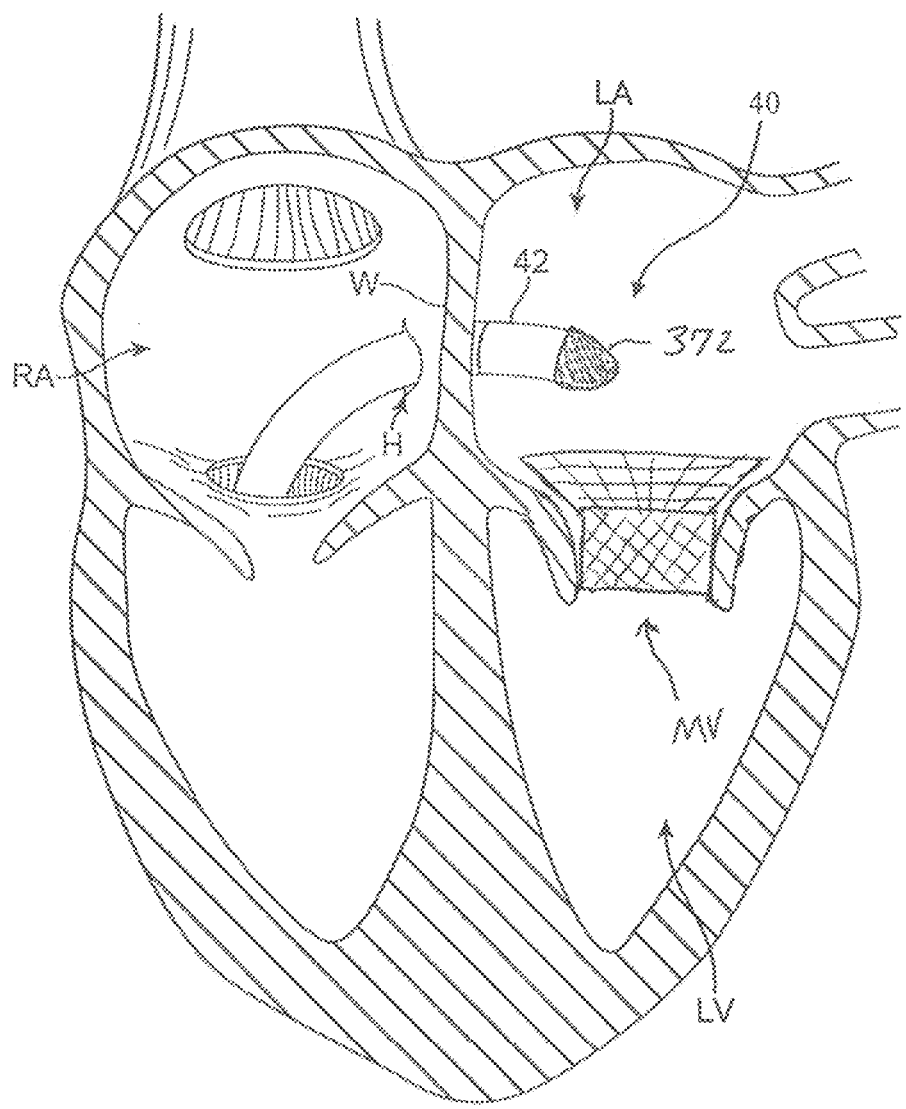

One example of a treatment procedure to be performed on the heart 30 is generally reflected by FIG. 27. A transcatheter delivery device 40 is shown after having been introduced into the vasculature via a percutaneous entry point (e.g., the Seldinger technique), and having been tracked through the vasculature and into the left atrium LA. For example, the percutaneous entry point may be formed in a femoral vein. Thereafter, a guidewire (not shown) assembly is advanced through the circulatory system, eventually arriving at the heart. The guidewire assembly is directed into the right atrium RA (e.g., via the vena cava), traverses the right atrium RA, and is made to puncture or otherwise pass through a hole H in the atrial septal wall W (e.g., with the aid of a transseptal needle), thereby entering the left atrium LA. Once the guidewire assembly is positioned, the delivery device 40 is tracked over the guidewire assembly and delivered transseptally to the left atrium LA. From the arrangement of FIG. 27, the elongated member 370 is manipulated, steered, and/or advanced as described above, directing the docking structure 372 through and beyond the mitral valve MV (FIG. 28). The guide member assembly 360 is then manipulated to dock the docking structure 372 to native anatomy. In some embodiments, the docking structure 372 can include one or more inflatable anchor members and/or one or more grip bodies as described above. In some embodiments, the docking structure 372 can be pressed deep into the left ventricle LV (e.g., at the apex A) and anchored or lodged into position as described earlier. The so-docked guide member assembly 360 provides a stable rail that the support shaft assembly 52 and the delivery sheath assembly 50 of the delivery device 40 can then be tracked over, bringing the capsule 42 into the mitral valve MV as in FIG. 29. Because the docking structure 372 is relatively fixed to the native anatomy, a push/pull tension can be applied to the elongated member 370 allowing the delivery device 40 to be more readily distally advanced over the elongated member 370. Further, because the elongated member 370 can be generally aligned with the mitral valve MV via the docked docking structure 372, the capsule 42 will be similarly directed into and aligned with the mitral valve MV. The delivery device 40 is then operated to retract capsule 42 to thereby deploy the prosthetic heart valve 400 at the mitral valve MV (FIG. 30). Following deployment of the prosthetic valve 400, the docking structure 372 is either released from the elongated member 370 or, as shown in FIG. 31, the elongated member 370 is retracted or advanced proximally within the inner shaft 354 to relocate the docking structure 372 at the distal end of the inner shaft 354. In addition, the capsule 42 is advanced back over the inner shaft 354 thereby reconfiguring the delivery device 40 from a deployed configuration or arrangement back into a delivery configuration or arrangement. Once the delivery device 40 has been reconfigured into a delivery configuration, the delivery device 40 is then removed from the patient.

The assemblies, systems and methods of the present disclosure provide a marked improvement over previous designs and techniques, for example in transcatheter delivery of a prosthetic mitral valve. By docking an elongated member or rail to native anatomy and utilizing the so-docked guide member assembly for advancing, tracking, or guiding the prosthetic heart valve delivery device to the target native mitral valve (e.g., a transseptal approach to the mitral valve from the left atrium), the anatomical complexities presented by transcatheter mitral valve delivery are addressed.

Although the present disclosure has been described with reference to preferred embodiments, workers skilled in the art will recognize that changes can be made in form and detail without departing from the spirit and scope of the present disclosure.

What is claimed is:

1. A method of delivering a prosthetic heart valve comprising:
    advancing a distal region of a guide member assembly into a heart;
    docking the distal region to native anatomy of the heart;
    advancing a delivery device over the docked guide member assembly, the delivery device carrying a collapsed prosthetic heart valve;
    tensioning the docked guide member assembly simultaneously with the step of advancing the delivery device;
    locating the collapsed prosthetic heart valve at an implantation site;
    deploying the prosthetic heart valve from the delivery device;
    removing the delivery device from the patient; and
    removing at least a portion of the guide member assembly from the patient.

2. The method of claim 1, wherein the native anatomy is a wall of the heart.

3. The method of claim 1, wherein the native anatomy is at least one heart valve leaflet.

4. The method of claim 1, wherein the native anatomy includes chordae.

5. The method of claim 1, wherein the native anatomy is a papillary muscle.

6. The method of claim 1, wherein the implantation site is a mitral valve.

7. The method of claim 1, wherein the step of removing at least a portion of the guide member assembly includes:
    undocking the distal region from the native anatomy; and
    removing an entirety of the guide member assembly from the patient.

8. The method of claim 1, wherein the guide member assembly includes an elongated member and a docking structure, the docking structure defining the distal region of the guide member assembly, and further wherein the step of removing at least a portion of the guide member assembly includes:
    releasing the elongated member from the docking structure; and
    removing the elongated member from the patient.

9. The method of claim 1, wherein the distal region comprises a docking structure including at least one anchor member selected from the group consisting of a clip, a hook, a screw, a barb, and a pincer.

10. The method of claim 1, wherein the distal region comprises a docking structure including first and second anchor arms, and further wherein the step of docking the distal region includes:
    docking the first anchor arm to a first wall of the heart; and
    docking the second anchor arm to a second wall of the heart opposite the first wall.

11. The method of claim 1, wherein the guide member assembly includes an elongated member, a docking structure connected to a distal end of the elongated member, and an outer sheath, the elongated member and docking structure slidably disposed within the outer sheath, and further wherein the step of advancing the distal region includes arranging the docking structure in a collapsed condition within the outer sheath, and even further wherein the step of docking the distal region includes:
    locating the docking structure distal the outer sheath such that the docking structure assumes a deployed condition; and
    docking the docking structure in the deployed condition to the native anatomy.

12. The method of claim 11, wherein the docking structure is configured to self-deploy from the collapsed condition to the deployed condition upon release from the outer sheath.

13. The method of claim 1, wherein the distal region comprises a docking structure including at least one inflatable anchor member comprising a balloon.

14. The method of claim 13, wherein the guide member assembly further includes a plurality of gripping members disposed on an exterior surface of the balloon, and further wherein the step of docking the distal region includes:
inflating the balloon to force the gripping members into engagement with the native anatomy.

15. The method of claim 13, wherein the step of removing at least a portion of the guide member assembly includes:
deflating the balloon.

16. The method of claim 13, wherein the deficient heart valve is a mitral valve and the native anatomy includes chordae.

17. The method of claim 1, wherein following the step of docking the distal region, the method further comprising:
applying electrical stimulation to the heart via the guide member assembly.

18. The method of claim 1, wherein the guide member assembly is provided as part of the delivery device, including the distal region of the guide member assembly configured to provide a nose cone of the delivery device in a delivery state.

19. The method of claim 1, wherein the guide member assembly includes an elongated member selected from the group consisting of a wire and a suture.

20. The method of claim 1, wherein the deficient valve is a mitral valve, and further wherein the step of advancing the distal region includes advancing the distal region to the native anatomy via a transseptal approach.

21. The method of claim 1, wherein the deficient valve is a mitral valve, and further wherein the step of advancing the distal region includes advancing the distal region to the native anatomy via a retrograde approach.

22. The method of claim 1, wherein the guide member assembly includes a steerable elongated member, and further wherein the steps of advancing the delivery device includes selectively deflecting the steerable elongated member.

23. The method of claim 1, wherein the guide member assembly includes a plurality of elongated members slidably disposed within an outer sheath, and further wherein the step of docking the distal region includes sequentially docking a distal segment of each of the plurality of elongated members to spaced locations of the native anatomy.

* * * * *